(12) United States Patent
McNaughton et al.

(10) Patent No.: US 9,400,249 B2
(45) Date of Patent: Jul. 26, 2016

(54) DETECTION OF BIOPOLYMER INTERACTIONS, CANCER CELLS, AND PATHOGENS USING SPLIT-SUPERCHARGED GFP

(71) Applicant: Colorado State University Research Foundation, Fort Collins, CO (US)

(72) Inventors: Brian R. McNaughton, Fort Collins, CO (US); Alex M. Chapman, Fort Collins, CO (US); Brett Blakeley, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 13/899,312

(22) Filed: May 21, 2013

(65) Prior Publication Data

US 2014/0011214 A1    Jan. 9, 2014

Related U.S. Application Data

(60) Provisional application No. 61/649,441, filed on May 21, 2012.

(51) Int. Cl.
*G01N 21/64*    (2006.01)
*G01N 33/574*    (2006.01)
*G01N 33/58*    (2006.01)

(52) U.S. Cl.
CPC ...... *G01N 21/6486* (2013.01); *G01N 33/57492* (2013.01); *G01N 33/582* (2013.01); *C07K 2319/60* (2013.01)

(58) Field of Classification Search
CPC .................................................... G01N 21/64
USPC ........................................................ 530/350
See application file for complete search history.

(56) References Cited

U.S. PATENT DOCUMENTS

2006/0257887 A1   11/2006   Waldo et al.
2009/0170069 A1   7/2009   Ghosh et al.
2012/0100569 A1   4/2012   Liu et al.

OTHER PUBLICATIONS

Barnard et al. 2008; Development and implementation of split-GFP-based bimolecular fluorescence complementation (BiFC) assays in yeast. Biochem. Soc. Trans. 36: 479-482.*
Lawrence et al. 2007; Supercharging proteins can impart unusual resilience. J. Am. Chem. Soc. 129(33): 1-8.*
Stepanenko et al. 2008; Fluorescent proteins as biomarkers and biosensors: throwing color lights on molecular and cellular processes. Curr Protein Pept Sci. 9(4): 338-369.*
Chu et al. (2014; Noninvasive intravital imaging of cellular differentiation with a bright red-excitable fluorescent protein. Nature Methods. 11(5): 572.*
Chu et al. (2014; Noninvasive intravital imaging of cellular differentiation with a bright red-excitable fluorescent protein. Nature Methods. 11(5): Supplemental Information.*
Prasher et al. 1992; Primary structure of the Aequorea Victoria green-fluorescent protein. Gene. 111: 229-233.*
PCT/US13/42078 International Search Report and Written Opinion mailed Oct. 2, 2013 (16 pages).
Karanicolas et al.; "A de novo Protein Binding Pair by Computational Design and Directed Evolution"; Mol. Cell. 22; Apr. 2011; vol. 42, No. 2; pp. 250-260.
Ghosh et al., "Antiparallel Leucine Zipper-Directed Protein Reassembly: Application to the Green Fluorescent Protein," *J. Am. Chem. Soc.*, vol. 122, 5658-5659 (2000).
Magliery et al., "Detecting Protein—Protein Interactions with a Green Fluorescent Protein Fragment Reassembly Trap: Scope and Mechanism," *J. Am. Chem. Soc.*, vol. 127, 146-157 (2005).
Sarkar et al., "Re-engineering a split-GFP reassembly screen to examine RING-domain interactions between BARD1 and BRCA1 mutants observed in cancer patients" (Abstract only), *Mol Biosyst.* 4(6):599-605 (Jun. 2008).
Thompson et al., "Engineering and Identifying Supercharged Proteins for Macromolecule Delivery into Mammalian Cells," *Methods Enzymol.* Author Manuscript. vol. 503: 293-319 (2012).

* cited by examiner

*Primary Examiner* — Karen Cochrane Carlson
(74) *Attorney, Agent, or Firm* — Polsinelli PC

(57) ABSTRACT

Systems and methods for detecting protein-protein interactions and/or detecting a targeted cell using a split supercharged protein reporter system are described.

23 Claims, 7 Drawing Sheets

```
-4_mNep,   1 MGEELIKENMHMKLYMEGTVNNHHFKCTSEGEGKPYEGTQTGRIKVVEGGPLPFAFDILA
+35_mNep,  1 MGERLIKEKMHMKLYMKGTVNNHKFKCTSKGKGKPYRGTQTGRIKVVRGGPLPFRFDILA

-4_mNep,  61 TCFMYGSKTFINHTQGIPDFFKQSFPEGFTWERVTTYEDGGVLTATQDTSLQDGCLIYNV
+35_mNep, 61 TCFMYGSKTFINKTQGRPDFFKQSFPEKFTWERVTTYEKGGVLTATQDTSLQDGCLIYNV

-4_mNep, 121 KIRGVNFPSNGPVMQKKTLGWEASTETLYPADGGLEGRCDMALKLVGGGHLICNLKTTYR
+35_mNep,121 KIRGVNFPSNKPVMQKKTLGWRASTKTLYPADGGLKGRCDMKLKLVGGGHLICNLKTTYR

-4_mNep, 181 SKKPAKNLKMPGVYFVDRRLERIKEADNETYVEQHEVAVARYCDLPSKLGHKLNGMDELY
+35_mNep,181 SKKPKKNLKMPGVYFVDRRLERIKEADNRTYVRQHEVAVARYCDLPSKLGHKLNGRKERY

-4_mNep, 241 K    [SEQ ID NO 20]
+35_mNep, 241 K   [SEQ ID NO 21]
```

FIG. 8

DETECTION OF BIOPOLYMER INTERACTIONS, CANCER CELLS, AND PATHOGENS USING SPLIT-SUPERCHARGED GFP

CROSS-REFERENCE TO RELATED APPLICATIONS

This application claims the benefit of U.S. Provisional Application No. 61/649,441, filed May 21, 2012, the disclosure of which is hereby incorporated by reference in its entirety.

FIELD OF THE INVENTION

The present disclosure relates to systems and methods for detecting protein-protein interactions and/or detecting a targeted cell using a split reporter protein system.

BACKGROUND OF THE INVENTION

The development of methods that rapidly and accurately identify interactions between structurally diverse proteins and/or peptides is key to advancing the growing field of proteomics. Identifying interactions involving structurally diverse proteins with broad biophysical properties is critical to expanding our understanding of complex cellular processes. Techniques such as immuno-precipitation, mass spectrometry, affinity purification, and protein microarrays have been used to identify interactions involving proteins and/or peptides in vitro. However, these approaches are laborious (typically requiring distinct expression and purification steps for each protein or peptide studied), low-throughput, are often limited to high-affinity interactions, and can involve complicated and/or expensive equipment. Perhaps most importantly, these methods do not provide any strong information on the likelihood of identified interactions occurring in vivo.

Popular in vivo approaches to identify and study interactions involving proteins and/or peptides include two-hybrid screening and split-protein reassembly. Common limitations of the two-hybrid screening approach include: the significant number of false positive results; the need for nuclear localization of the interacting proteins or peptides; and the need for transcription and translation of the reporter protein, which increases the overall length and complexity of the two-hybrid screening approach.

Split-protein reassembly has been used as an alternative to two-hybrid methods to identify and study protein-protein interactions within prokaryotic and eukaryotic cells using a reporter protein that is split into two fragments and fused to possible interacting peptide and/or protein partners in the protein-protein interaction of interest. In the absence of fused binding partners, the split-reporter fragments do not reassemble and reporter activity is not observed. However, if the interacting peptide and/or protein partners have sufficient affinity for one another, the resulting protein-protein interaction brings the two fragments of the split reporter protein, resulting in the reassembly of a functional reporter protein and associated reporter activity.

In general, reporter proteins typically fluoresce, catalyze a colorimetric or fluorescent reaction, or endow a host cell with resistance to an exogenous toxin. Split-reporter proteins currently used to detect protein-protein interactions in bacteria, *S. cerevisiae*, and mammalian cells include β-lactamase, β-galactosidase, dihydrofolate reductase, ubiquitin, and Green Fluorescent Protein (GFP). GFP is a particularly well-suited split-reporter protein for at least several reasons. GFP does not require the addition of exogenous reagents in order to generate a signal. In addition, GFP expresses, folds, and fluoresces in a large number of cell types and intracellular compartments, and is generally resistant to proteolytic degradation in vivo. Further, the formation of a fluorescent chromophore in GFP is an irreversible reaction, enhancing the ability of reassembled GFP reporter protein to detect weak protein-protein interactions with dissociation constants ($K_d$) as high as 1 mM.

However the use of GFP as a split-reporter protein is not without some limitations. The fragments of the split GFP reporter protein may be susceptible to instability and aggregation within the cell during use. Some existing split-GFP reporter proteins, such as split-sg100 GFP, incorporate enhanced-stability GFP variants. Even using these enhanced-stability GFP variants, interaction-dependent reassembly screens using split-sg100 GFP fusions may be performed well below physiological temperature (typically 20° C.-30° C.) to further enhance fragment stability to acceptable levels. However, the results of interaction-dependent reassembly screens conducted at reduced temperatures may not be applicable at physiological temperatures due to the sensitivity of protein-protein interactions to changes in ambient temperature. In addition, existing stabilized split-GFP reporter proteins, such as split-sg100 GFP, may requires 24-72 hours in order to generate visible levels of cellular GFP fluorescence.

A need exists for a split-reporter protein in which the protein fragments are stabilized and resistant to aggregation at physiological temperatures. In addition, a need exists for a robust split-reporter protein capable of interaction-dependent reassembly under a variety of conditions and further capable of generating a reporting signal in a relatively short time.

BRIEF SUMMARY OF THE INVENTION

The present disclosure provides a method for detecting a protein-protein interaction in vivo, the method including providing a split-supercharged GFP reporter that includes a C-terminal supercharged GFP fragment and an N-terminal supercharged GFP fragment; fusing the C-terminal supercharged GFP fragment with a first interacting protein and fusing the N-terminal supercharged GFP fragment with a second interacting protein; introducing the C-terminal supercharged GFP fragment fused to the first interacting protein and the N-terminal supercharged GFP fragment fused to the second interacting protein into a cell; incubating the cell; and measuring a fluorescence signal indicating the protein-protein interaction between the first interacting protein and the second interacting protein within the cell. In this aspect, the protein-protein interaction induces a reassembly of the C-terminal supercharged GFP fragment and the N-terminal supercharged GFP fragment and the reassembled C-terminal supercharged GFP fragment and N-terminal supercharged GFP fragment produces the fluorescence signal. The split-supercharged GFP reporter may be a split-superpositive GFP (spGFP) reporter comprising a C-terminal spGFP fragment and an N-terminal spGFP fragment in one aspect. The C-terminal spGFP fragment may have a net theoretical charge of +10 and the N-terminal spGFP fragment may have a net theoretical charge of +24. The method may be performed under physiological conditions. The method may be performed at a temperature of about 37° C., or the method may be performed at a temperature of less than 37° C. The fluorescence signal may be measured by flow cytometry or by picking fluorescent colonies. The fluorescence signal may be measured from about 1 hour to about 24 hours after introducing the C-terminal supercharged GFP fragment fused to the first interacting protein and the N-terminal supercharged GFP fragment fused to the second interacting protein into the cell. The C-terminal supercharged GFP fragment fused to the first interacting protein and the N-terminal supercharged GFP fragment fused to the second interacting protein may be proteins. Alternatively, the C-terminal supercharged GFP fragment fused to the first interacting protein and the N-terminal supercharged GFP fragment fused to the second interacting protein may be nucleic acids. The first interacting protein and the second interacting protein may be corresponding leucine zipper peptides. Alternatively, the first interacting protein may be Pdar and the second interacting protein may be Prb.

In another aspect, the present disclosure provides a split-supercharged GFP reporter for the detection of protein-protein interactions in vivo. The reporter may include C-terminal supercharged GFP fragment and an N-terminal supercharged GFP fragment. The C-terminal supercharged GFP fragment may have a theoretical net charge ranging from about −4 to about +10 and the N-terminal supercharged GFP fragment may have a theoretical net charge ranging from about −4 to about +24. Alternatively, the C-terminal supercharged GFP fragment may have a theoretical net charge of about +10 and the N-terminal supercharged GFP fragment may have a theoretical net charge of about +24. The C-terminal supercharged GFP fragment may be fused to a first interacting protein and the N-terminal supercharged GFP fragment may be fused to a second interacting protein. The first interacting protein and second interacting protein may be complementary proteins in the protein-protein interaction. The C-terminal supercharged GFP fragment and the N-terminal supercharged GFP fragment may be proteins. Alternatively, the C-terminal supercharged GFP fragment and the N-terminal supercharged GFP fragment may be nucleic acids encoding the split-supercharged GFP reporter.

In another aspect, the present disclosure provides a method of detecting a targeted cell. The method may include providing a split-superpositive reporter that may include a C-terminal reporter fragment fused to a first targeting protein and an N-terminal reporter fragment fused to a second targeting protein. This method may also include contacting the split super positive reporter with the targeted cell and detecting a signal produced by a reassembly of the split-superpositive reporter on a surface of the targeted cell. The reassembly of the split-superpositive reporter may occur when the first targeting protein binds to a first targeting moiety situated on a surface of the targeted cell, and the second targeting protein binds to a second targeting situated on the surface of the targeted cell. The targeted cell may be a cancer cell chosen from: a cholangiocarcinoma cell, a prostate cancer cell, a breast cancer cell, a neuroblastoma cell, an osteosarcoma cell, a head cancer cell, a neck cancer cell, and a breast cancer cell. The targeted cell may also be chosen from: a HER-2 positive breast cancer cell and a PC-3 human prostate cancer cell. The first targeting moiety and the second targeting moiety may be different cell surface structures from: a membrane receptor, a membrane transport protein, a membrane enzyme, a cell adhesion molecule, and a cell wall structural compound. The first targeting protein may bind specifically to the first targeting moiety and the second targeting protein binds specifically to the second targeting moiety. The combination of the first targeting moiety and the second targeting moiety may specifically identify the targeted cell. Additionally in the method, the reassembly of the split-superpositive reporter may include fusing the C-terminal reporter fragment and the N-terminal reporter fragment to form a functional reporter protein. The functional reporter protein may be chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). In particular, the functional reporter protein may be a spGFP, the C-terminal reporter fragment may be a C-terminal spGFP fragment and the N-terminal reporter fragment may be an N-terminal spGFP fragment. The C-terminal spGFP fragment and the N-terminal spGFP fragment may be situated on surface of the targeted cell membrane prior to reassembly of the spGFP, and the spGFP may be transferred into a cytoplasm of the targeting cell after reassembly on the surface of the targeted cell. The C-terminal spGFP fragment may further include a theoretical net charge ranging from about +5 to about +30, the N-terminal spGFP fragment may further include a theoretical net charge ranging from about +5 to about +30; and the reassembled spGFP may further include a theoretical net charge ranging from about +5 to about +30.

In another aspect, the present disclosure provides a split-superpositive reporter for detecting a targeted cell. The split-superpositive reporter may include a C-terminal reporter fragment fused to a first targeting protein and an N-terminal reporter fragment fused to a second targeting protein. The first targeting protein may bind specifically to a first targeting moiety situated on a surface of the targeting cell and the second targeting protein may bind specifically to a second targeting moiety situated on the surface of the targeting cell. The split-superpositive reporter may reassemble into a functional superpositive reporter protein when the first targeting protein binds to the first targeting moiety and the second targeting protein binds to the second targeting moiety on the surface of the targeted cell. The functional superpositive reporter protein may be chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune). The functional superpositive reporter protein may be a spGFP, the C-terminal reporter fragment may be a C-terminal spGFP fragment and the N-terminal reporter fragment may be an N-terminal spGFP fragment. The C-terminal spGFP fragment may further include a theoretical net charge ranging from about +5 to about +30, the N-terminal spGFP fragment may further include a theoretical net charge ranging from about +5 to about +30, and the spGFP may further include a theoretical net charge ranging from about +5 to about +30.

BRIEF DESCRIPTION OF THE DRAWINGS

The following drawings illustrate various aspects of the disclosure.

FIG. 8 is a table comparing the protein sequences of mNeptune (−4_mNep) and superpositive mNeptune (+35_mNep).

Corresponding reference characters and labels indicate corresponding elements among the views of the drawings. The headings used in the figures should not be interpreted to limit the scope of the claims.

DETAILED DESCRIPTION

Figure 1:
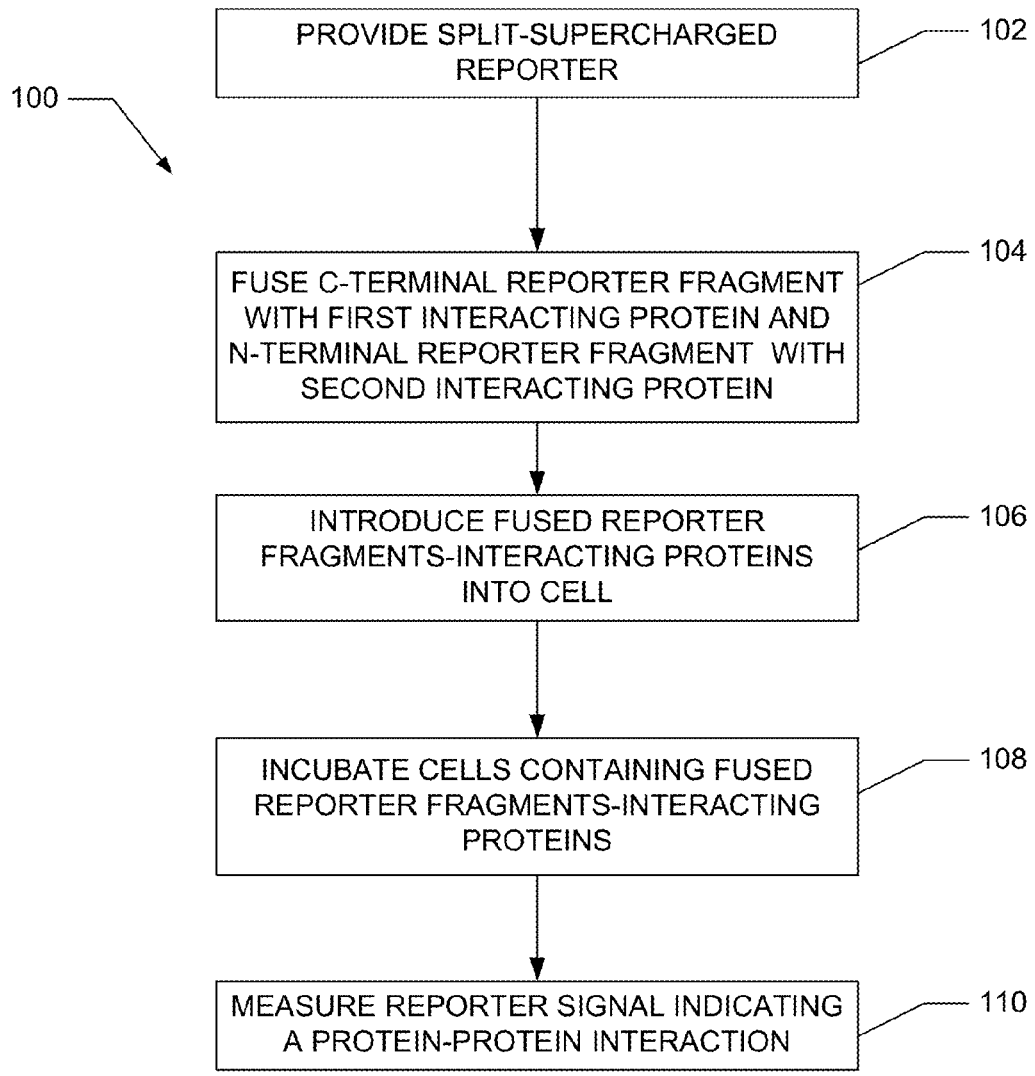
FIG. 1 is a flow chart summarizing a method of detecting a protein-protein interaction using a split-supercharged reporter.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present disclosure are generally performed according to conventional methods well known in the art and as described in various general and more specific references that are cited and discussed throughout the present specification unless otherwise indicated. Enzymatic and staining reactions, and purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also those well known and commonly used in the art. Standard techniques are used for chemical syntheses, chemical analyses, pharmaceutical preparation, formulation, and delivery, and diagnosis and treatment of patients.

Multiple aspects of systems and methods for detecting a protein-protein interaction and/or detecting a targeted cell are disclosed herein, which make use of split supercharged reporter proteins. As will be realized, the disclosed aspects are capable of modifications in various aspects, all without departing from the spirit and scope of the present disclosure. Accordingly, all sections of the present disclosure, including the Summary, Drawings and Detailed Description are to be regarded as illustrative in nature and not restrictive.

In various aspects, the present disclosure systems and methods for detecting a protein-protein interaction and/or detecting a targeted cell that make use of split supercharged reporter proteins. The split supercharged reporter proteins may be split into two or more fragments and fused with interacting proteins that potentially participate in a protein-protein interaction, or alternatively the split supercharged reporter proteins may be fused to one or more targeting moieties that bind to exposed surface proteins on a targeted cell.

The split supercharged reporter protein may be derived from an engineered variant of a reporter protein that incorporates a relatively large number of charged and solvent-exposed residues that impart a net positive or net negative theoretical charge on the functional supercharged reporter protein. Net theoretical charge, as defined herein, refers to the estimated net charge of a protein based on the number and types of residue containing charged side groups. The supercharged reporter protein may be split into a C-terminal reporter fragment and an N-terminal reporter fragment to produce the split supercharged reporter protein. The C-terminal reporter fragment and the N-terminal reporter fragment may also carry a net positive or negative theoretical charge, like the assembled supercharged reporter protein. The unique properties of the split supercharged reporter protein in various aspects overcome many of the limitations of existing split reporter protein systems.

The net positive or negative charges of the C-terminal reporter fragment and the N-terminal reporter fragment of the split supercharged reporter protein enhance the solubility of these proteins and further reduce the susceptibility of the reporter fragments to aggregation during in vivo use. Without being limited to any particular theory, it is well-known in the art that protein solubility tends to decrease as a protein reaches its isoelectric point, defined herein as those conditions including, but not limited to, pH under which a protein bears no net charge. Further, the net charges of peptide variants within a protein are known to be a reliable predictor of the susceptibility of a protein to aggregation. For example, intrinsically disordered proteins, which often possess large positive or negative theoretical net charges, are known to resist aggregation within a cell and typically remain unfolded.

These advantages of the split supercharged reporter protein are accomplished with minimal impact on other essential characteristics of the supercharged reporter protein including, but not limited to, the signaling activity of the folded supercharged reporter protein formed by the reassembly of the C-terminal reporter fragment and the N-terminal reporter fragment. It is well-known in the art that the function of a protein is sensitive to the three-dimensional folded tertiary structure of the protein, which in turn is influenced by the interaction of charged side chains within the protein's amino acid sequence. It was unexpectedly discovered that the theoretical net charges of the C-terminal reporter fragment and the N-terminal reporter fragment of the split supercharged reporter protein could be increased to levels as high as about +24 or higher with virtually no impact on the reassembly of the reporter fragments or the subsequent generation of a reporting signal by the reassembled supercharged reporter protein.

It was also unexpectedly discovered that the net theoretical charges of the C-terminal reporter fragment and an N-terminal reporter fragment combine synergistically to render the reassembled supercharged reporter protein capable of penetrating a targeted cell membrane. The supercharged C-terminal reporter fragment and N-terminal reporter fragment, neither of which is capable of spontaneously penetrating a targeted cell membrane, were found to reassemble and refold into the functional supercharged reporter protein, which spontaneously penetrated the targeted cell. Because this reassembly of the reporter fragments is an irreversible process, the reporter signal accumulates within the targeted cell as more and more reporter fragments reassemble on the targeted cell's surface and penetrate the targeted cell.

Without being limited to any particular theory, it is known in the art that the penetration of a cell by a protein may be mediated by a combination of protein folding and a net positive theoretical charge of the protein. Thus, a folded protein with a sufficiently high net theoretical positive charge may penetrate a targeted cell. By contrast, neither a folded protein lacking a sufficiently high net theoretical positive charge nor a non-folded protein with a high net theoretical positive charge may be capable of penetrating a targeted cell in many circumstances. The C-terminal reporter fragment and an N-terminal reporter fragment are typically unfolded and therefore are less likely to penetrate a targeted cell as separate fragments. However, the reassembled supercharged reporter protein not only possesses the combined net theoretical charge of the reporter fragments, but also folds into a functional three-dimensional tertiary structure upon reassembly. The combined high positive theoretical charge and folded structure of the reassembled supercharged reporter protein readily penetrates the targeted cell.

The split supercharged reporter proteins in various aspects represent a fundamentally new class of reagents for the detection of targeted cells including, but not limited to various cancer cells. The C-terminal reporter fragment and an N-terminal reporter fragment, which are fused to one or more targeting proteins are brought into close proximity through the preferential binding of the targeting proteins to one or more targeting moieties situated on the surface of a targeted cell. The irreversible reassembly of the supercharged reporter protein by the fusing of the reporter fragments triggers the folding and signal generation by the supercharged reporter protein as well as the penetration of the functional supercharged reporter protein into the targeted cell. Because the transfer of the supercharged reporter protein into the targeted cell is directly fused to the reporter's activation, the only detectable reporter signals originate from within targeted cells. This unique feature of the split supercharged reporter protein improves bioimaging by increasing signal-to-noise.

Various aspects of the split supercharged reporter protein, as well as systems and methods for detecting a protein-protein interaction and/or for detecting a targeted cell, are described in further detail herein below.

Split Supercharged Reporter

Split supercharged reporters include a supercharged reporter protein that has been split into two fragments: a C-terminal supercharged protein fragment and an N-terminal supercharged protein fragment. In an aspect, the supercharged reporter protein, C-terminal supercharged protein fragment, and N-terminal supercharged protein fragment are all characterized by a net theoretical charge.

In various aspects, the C-terminal and N-terminal supercharged protein fragments are each fused to an additional protein to form the split supercharged reporter. The additional protein may be any one of at least several proteins depending on the intended use of the split supercharged reporter. In one aspect, if the split supercharged reporter is to be used to detect a protein-protein interaction, the C-terminal supercharged protein fragment may be fused to a first interacting protein and the N-terminal supercharged protein fragment may be fused to a second interacting protein; the first interacting protein and the second interacting protein may participate in a protein-protein interaction to be detected by the split supercharged reporter within a cell. In another aspect, if the split supercharged reporter is to be used to detect a targeted cell, the C-terminal supercharged protein fragment and the N-terminal supercharged protein fragment may be fused to a one or more targeting proteins; the one or more targeting proteins may preferentially bind to one or more targeting moieties exposed on the surface of a cell membrane of a targeted cell.

Supercharged Reporter Protein

The supercharged reporter protein from which the supercharged split reporter is derived may be a supercharged variant of any known reporter protein without limitation. "Reporter protein", as used herein, refers to any protein capable of generating a detectable signal within a cell. Reporter proteins typically fluoresce, catalyze a colorimetric or fluorescent reaction, or endow a host cell with resistance to an exogenous toxin. Any fluorescent protein may be used without limitation provided that the protein is substantially inactive (does not fluoresce) when fragmented into two or more fragments. Non-limiting examples of reporter proteins that fluoresce include green fluorescent proteins (GFP), red fluorescent proteins (YFP), yellow fluorescent proteins (YFP), blue fluorescent proteins such as TagBFP (Evrogen), cyan fluorescent proteins, yellow fluorescent proteins, orange fluorescent proteins, and far-red fluorescent proteins such as mNeptune. Non-limiting examples of green fluorescent proteins include: mTagBFP2 (Evrogen), EGFP, Emerald, Superfolder GFP, Monomeric Azami Green (MBL International), TagGFP2 (Evrogen), mUKG, mWasabi (Allele Biotech), Clover, and mNeonGreen (Allele Biotech). Non-limiting examples of red fluorescent proteins include: mRaspberry, mCherry, mStrawberry, mTangerine, tdTomato, TagRFP (Evrogen), TagRFP-T, maple, mRuby, and mRuby2. Non-limiting examples of cyan fluorescent proteins include: monomeric Midoriishi-Cyan (MBL International); Tag CFP (Evrogen); and mTFP1 (Allele Biotech). Non-limiting examples of yellow fluorescent proteins include: EYFP, Citrine, Venus, SYFP2, and TagYFP (Evrogen). The sequences of fluorescent proteins, their characteristics (e.g., excitation and emission wavelengths, extinction coefficients, brightness and pKa) are generally detailed in the source literature well known to those of routine skill in the art.

Non-limiting examples of reporter proteins that catalyze a colorimetric or fluorescent reaction include luciferase. Non-limiting examples of proteins that endow a host cell with resistance to an exogenous toxin include dihydrofolate reductase (DHFR), β-lactamase, and β-galactosidase.

In one aspect, the supercharged reporter protein is a supercharged green fluorescent protein (scGFP) derived from a green fluorescent protein (GFP). scGFP may possess at least several characteristics that enhance its effectiveness as a split supercharged reporter protein. Unlike other enzymatic reporter proteins that catalyze the formation of a fluorescent or colorimetric molecule from a precursor, or catalyze the degradation of an exogenous toxin, scGFP does not require the addition of exogenous reagents in order to generate a signal. In addition, scGFP expresses, folds, and fluoresces in a large number of cell types and intracellular compartments, and is generally resistant to proteolytic degradation. Since the formation of a fluorescent chromophore in scGFP is irreversible, split-scGFP reassembly can be used to examine weak interactions with dissociation constants ($K_d$) as high as 1 mM.

In another aspect, the supercharged reporter protein is a supercharged far-red fluorescent protein (sc-mNeptune). sc-mNeptune is structurally related to scGFP and has all of the favorable characteristics of scGFP except that supercharged mNeptune fluoresces efficiently when excited at 633 nm, a wavelength commonly used for imaging. This excitation wavelength is particularly advantageous because it transmits more efficiently though body tissues, which are relatively opaque to light at wavelengths of less than about 600 nm due to absorption by hemoglobin. In addition, the fluorescence produced by the supercharged mNeptune reporter protein may be observed using a standard Cy5 filter. The use of the split supercharged mNeptune reporter in this aspect makes possible bioimaging in the deep tissues of whole mammals.

"Supercharged reporter protein", as referred to herein, refers to any highly mutagenized variant of a neutral reporter protein with a relatively high theoretical negative or positive charge that is resistant to aggregation, among other advantageous properties. In one aspect, a neutral reporter protein with a relatively small net theoretical charge, defined herein as a theoretical charge magnitude of less than about 5, is mutegenized by substituting one or more positively-charged or negatively-charged amino acids into the amino acid sequence of the neutral reporter protein. In an aspect, a positively-charged amino acid may be substituted for a neutral or negatively-charged amino acid to increase the net positive theoretical charge of a reporter protein. In another aspect, a negatively-charged amino acid may be substituted for a neutral or positively-charged amino acid to increase the magnitude of negative net theoretical charge of a reporter protein. The substitution of a positively-charged amino acid for a negatively-charged amino acid, or vice versa, results in a larger change in net theoretical charge magnitude than a substitution for a neutral amino acid.

Non-limiting examples of positively-charged amino acids include arginine (R), lysine (K), and to a limited extent histidine (H) at pH values of less than about 6. Non-limiting examples of negatively-charged amino acids include aspartic acid (D) and glutamic acid (E).

In an aspect, the supercharged reporter protein may have a net negative theoretical charge ranging from about −50 to about −5. In another aspect, the supercharged reporter protein may have a net positive theoretical charge ranging from about +5 to about +50. The magnitude of the net theoretical charge may influence one or more characteristics of the supercharged reporter protein including, but not limited to the protein's susceptibility to aggregation within a cell, the solubility of the protein, the stability of the protein, and any combination thereof. In one additional aspect, the magnitude of positive net theoretical charge may further influence the ability of the supercharged reporter protein to penetrate a targeted cell after reassembly of the reporter protein fragments on the surface of the targeted cell membrane. In another additional aspect, the net theoretical charge of the supercharged reporter protein may influence the characteristics of the C-terminal and N-terminal reporter fragments, as described herein below.

Any number of amino acid substitutions may be performed to obtain a highly mutegenized and supercharged variant of a relatively neutral reporter protein, so long as the folded conformation of the functional reporter protein is conserved. In one aspect, if the split supercharged reporter is derived from a GFP reporter protein, amino acid substitutions may be performed at up to about 29 positions. In another aspect, if the split supercharged reporter is derived from a mNeptune reporter protein, amino acid substitutions may be performed at up to about 25 positions.

In an aspect, the amino acid substitutions may be situated within the protein's overall sequence such that the substituted amino acid is situated in an exposed outer position when the reporting protein in a folded and functional conformation. In another aspect, the location of the amino acid substitution within the protein's overall sequence may be selected to minimize any changes to the reporter protein's folded and functional conformation, changes to the signaling activity of the functional reporter protein, changes to the ability of the functional reporter protein to penetrate into the target cell, or any combination thereof. For example, if the reporter protein is a fluorescent protein such as green fluorescent protein (GFP), a superpositive GFP (spGFP) may produce essentially the same intensity of fluorescence as a wild-type (i.e. neutrally-charged) GFP.

Reporter Fragments

In various aspects, the split supercharged reporter includes the C-terminal reporter fragment and the N-terminal reporter fragment derived from the supercharged reporter protein. In an aspect, both reporter fragments carry a relatively high magnitude of net theoretical charge due to the high magnitude of net theoretical charge carried by the supercharged reporter protein. In an aspect, the magnitude of net theoretical charge of the C-terminal reporter fragment and the N-terminal reporter fragment may each range from about 5 and about 30.

The relatively high magnitude of net theoretical charge of the reporter fragments imparts at least several useful characteristics including but not limited to: enhanced resistance to aggregation and enhanced solubility relative to uncharged reporter fragments derived from neutral reporter proteins, and any combination thereof. These characteristics may enhance the availability of the reporter fragments for induced reassembly of the reporter fragments into the functional supercharged reporter protein either on the cell membrane surface of the targeted cell during the detection of the targeted cell or within the cell during the detection of a protein-protein interaction. In addition, the enhanced solubility of the reporter fragments may enhance the solubility of the interacting proteins that may be fused to the reporter fragments, thereby expanding the scope of protein-protein interactions that are detectable using the split supercharged reporter to interacting proteins or peptides that are themselves susceptible to aggregation.

However, the net theoretical charge of each of the reporter fragments may be limited by one or more of at least several considerations. In one aspect, if one or both of the reporter fragments carries too high of a net theoretical charge, the electrostatic repulsion may have an inhibitory effect on the association rate of the reporter fragments, resulting in slower reassembly of the supercharged reporter protein and the generation of the reporting signal associated with the detection of a protein-protein interaction or targeted cell. In another aspect, if the split supercharged reporter is to be used to detect a targeted cell, a highly charged reporter fragment may bind indiscriminately to any oppositely-charged targeting moieties exposed on the surface of any cell via electrostatic forces and overwhelming the specific binding affinity of the fused targeting protein. In an additional aspect, if the net theoretical charge of a reporter fragment has an excessively large positive value, the reporter fragment may spontaneously penetrate into the targeted cell without reassembling into the supercharged reporter protein. In this additional aspect, the spontaneous penetration of a reporter fragment may reduce the availability of the reporter fragment for reassembly, thereby reducing the efficiency of reassembly and penetration of the functional split supercharged reporter.

In one aspect, the magnitude of the net theoretical charge of each of the C-terminal reporter fragment and the N-terminal reporter fragment may range from about 5 to about 25. In another aspect, if the split supercharged reporter is a split superpositive GFP (split-spGFP), the C-terminal split spGFP fragment may have a net theoretical charge ranging from about +5 to about +15. In this other aspect, the N-terminal split spGFP fragment may have a net theoretical charge ranging from about +5 to about +25. Without being restricted to any particular theory, it is believed that the split-superpositive GFP (split-spGFP) fragments with theoretical net charges below about +25 do not have the charge magnitude to appreciably penetrate mammalian cells at concentrations as low as 1-10 nM.

The relative sizes of the C-terminal reporter fragment and the N-terminal reporter fragment may be influenced by one or more of at least several factors. Non-limiting examples of factors influencing the relative size of the reporter fragments include: the location of the cleavage along the intact supercharged reporter protein's peptide sequence performed to separate the supercharged reporter protein into the reporter fragments; the location and/or density of charged amino acid substitutions along the intact supercharged reporter protein's peptide sequence; the solubility and/or aggregation susceptibility of each of the reporter fragments; the tendency of a reporter fragment to fold into a three-dimensional tertiary structure; and any combination thereof. In one aspect, the C-terminal reporter fragment and the N-terminal reporter fragment may be relatively equal in sequence length and net theoretical charge, resulting in relatively uniform characteristics including, but not limited to: solubility, resistance to aggregation, movement within the cell, movement over the surface of the cell membrane of the targeted cell, and any combination thereof.

In one aspect, the location along the supercharged reporter protein at which cleavage into the reported fragments occurs may be selected based on one or more of at least several factors including, but not limited to: maintaining a sufficient affinity for reassembly of the reporter fragments into the supercharged reporter protein; minimizing the impact of the cleavage on the tertiary structure of the reassembled supercharged reporter protein and/or the activity of the functional reassembled reporter protein; minimizing the influence of the fused interacting proteins and/or targeting proteins on the affinity for reassembly of the reporter fragment; minimizing the influence of the fused interacting proteins and/or targeting proteins on the tertiary structure of the reassembled supercharged reporter protein and/or the activity of the functional reassembled reporter protein; and any combination thereof.

In an aspect, the cleavage site of the intact supercharged reporter protein may be within an exposed external feature of the folded, functional reporter protein to form the reporter fragments. Non-limiting examples of suitable external features for cleavage of the intact reporter protein include external loops. The identification of a suitable cleavage site may be informed by characterization of the proposed cleavage site using techniques such as limited proteolysis, circular permutation, and loop insertions. In one aspect, if the intact reporter protein is scGFP, the cleavage site may be between amino acids 157 and 158 within an external loop. In this aspect, the external loop in the vicinity of the cleavage site may tolerate the insertion of up to about 20 amino acids without compromising the function of the reassembled functional reporting protein.

In one aspect, the supercharged reporter protein is superpositive green fluorescent protein (spGFP) that includes 231 amino acid residues and has a net theoretical charge of +34. In this aspect, the spGFP is cleaved into an N-terminal fragment that includes amino acids 1-157 and carries a net theoretical charge of +24, as well as a C-terminal fragment that includes amino acids 158-231 and carries a net theoretical charge of +10.

By way of non-limiting example, the N-terminal fragment of the spGFP (N-spGFP) may have the following protein sequence [SEQ ID NO. 22]: MGHHHHHHGGASKGER-LFRGKVPILVELKGDVNGHKFS-VRGEGKGDATRGKLTLK FICTTGKLPVPWPTLVTTL-TYGVQCFSRYPKHMKRHDFFKSAMPKGYVQERTI-SFKK DGKYKTRAEVKFEGRTLVNRIKLKGRD-FKEKGNILGHKLRYNFNSHKVYITADKR. By way of non-limiting example, the C-terminal fragment of the spGFP (C-spGFP) may have the following protein sequence [SEQ ID NO. 23]: KNGIKAKFKIRHNVKDGS-VQLADHYQQNTPIGRGPVLLPRNHYL-STRSKLSKDPKEK RDHMVLLEFVTAAGIKH-GRDERYK.

Proteins Fused to Reporter Fragments

In various aspects, the C-terminal reporter fragment and the N-terminal reporter fragment are fused with one or more proteins, depending on the intended use of the split supercharged reporter. In one aspect, if the split supercharged reporter is used to detect a protein-protein interaction, the C-terminal reporter fragment is fused with a first interacting protein and the N-terminal reporter fragment is fused with a second interacting protein. In this aspect, the first interacting protein and the second interacting protein participate in a protein-protein interaction of interest that is detected by the split protein reporter.

The first and second interacting proteins may be any proteins capable of participating in a protein-protein interaction. Non-limiting examples of protein-protein interactions include covalent binding of the first protein and second protein, non-covalent association of the first protein and the second protein, and any combination thereof. "Covalent binding", as used herein, refers to the formation of an interatomic bond characterized by the sharing of at least one electron. "Non-covalent association", as used herein, refers to a molecular interaction that does not involve an interatomic bond. Non-limiting examples of non-covalent associations include ionic bonding, hydrogen bonding, hydrophobic interactions, and attractions due to van der Waals forces.

Non-limiting examples of first and second interacting proteins suitable for fusion with the C-terminal reporter fragment and the N-terminal reporter fragment, respectively include: antigen-antibody pairs, ligand/receptor pairs, antagonists/inhibitors and corresponding proteins, enzyme/substrate pairs, parallel leucine zipper proteins, antiparallel leucine zipper proteins, DNA/RNA binding protein and corresponding DNA/RNA sequences, DNA/RNA binding proteins targeted to adjacent DNA/NA sequences, and any other known interacting protein pair. In another aspect, the C-terminal reporter fragment and the N-terminal reporter fragment may be fused with a carbohydrate and the remaining reporter fragment may be fused with a protein, in which the carbohydrate and the protein form a carbohydrate/protein binding pair.

In one aspect, the first and second interacting proteins may be a single pair that participates in a protein-protein interaction to be detected by the split supercharged reporter. In another aspect, the first interacting protein may be a target protein and the second interacting protein may be a member of a library of candidate proteins. In this aspect, the N-terminal or C-terminal reporter fragment may be fused with the target protein, and the multiple copies of the corresponding C-terminal or N-terminal reporter fragments may be fused with each of the second interacting proteins in the library of candidate proteins and each split supercharged reporter may be analyzed in a high-throughput fashion to identify the affinity of each candidate protein in the library for interacting with the target protein. Other candidate protein libraries may be analyzed in a similar fashion including, but not limited to: DNA/RNA binding sequences in a library used to determine the location of a target DNA/RNA sequence relative to known locations of DNA/RNA sequences corresponding to the DNA/RNA binding sequences in the library; candidate compounds in a library used to assess the binding affinity of the candidate compounds to a target receptor or other target protein; and any other known library of compounds of interest in a protein-protein or carbohydrate-protein interaction.

In another aspect, if the split supercharged reporter is used to detect a targeted cell, the C-terminal reporter fragment and the N-terminal reporter fragment are fused with at least one targeting protein. The targeted cell may be any mammalian cell including, but not limited to a cancer cell, an immune system cell, and any other mammalian cell of interest. Non-limiting examples of cancer cells suitable for use as targeted cells include: cholangiocarcinoma cells, prostate cancer cells, breast cancer cells, neuroblastoma cells, osteosarcoma cells, hepatocellular carcinoma cells, head cancer cells, neck cancer cells, and any other known cancer cells. Non-limiting examples of specific cancer cells include PC-3 human prostate cancer cells and HER-2+ breast cancer cells. Non-limiting examples of immune system cells include: phagocytes such as macrophages, neutrophils, and dendritic cells; mast cells; eosinophils; basophils; natural killer cells; B cells; and T cells such as killer T cells, helper T cells, and γδ T cells. The immune cells may further include immune cells at a particular activation state in various aspects.

In an aspect, the targeting protein may be any peptide, protein, antibody, or antibody fragment capable of binding to a targeting moiety; the targeting moiety in this aspect may include any protein, protein fragment, peptide, or amino acid situated upon or within a cell membrane of the targeted cell. The targeting peptide may be any sequence of amino acids with an affinity for binding a targeting moiety of a targeted cell. The number of amino acids in the targeting peptide sequence in this aspect may range from about 5 amino acids to about 20 amino acids. Non-limiting examples of peptide sequences suitable for use as a targeting protein are provided in Table 1 herein. Non-limiting examples of proteins or protein fragments suitable for use as targeting proteins include nucleic acid aptamers, antibodies, and antibody fragments. Non-limiting examples of proteins suitable for use as targeting proteins are provided in Table 2 herein.

TABLE 1

Cell Targeting Peptides

| Peptide Sequence | Targeted Cell Type | Size (kDa) | Approximate affinity (Kd in nM) |
|---|---|---|---|
| TPVLETPKLLLW [SEQ ID NO. 1] | Cholangiocarcinoma | 1.5 | 500 |
| FRPNRAQDYNTN [SEQ ID NO. 2] | Prostate cancer | 1.5 | 180 |
| VPWMEPAYQRFL [SEQ ID NO. 3] | Breast cancer, Neuroblastoma | 1.5 | 50,000-80,000 |
| ASGALSPSRLDT [SEQ ID NO. 4] | Osteosarcoma | 1.5 | 2000 |
| AGKGTPSLETTP [SEQ ID NO. 5] | Hepatocellular carcinoma | 1.5 | 50 |
| TSPLNIHNGQKL [SEQ ID NO. 6] | Head and neck cancer | 1.5 | 1000 |

TABLE 2

Cell Targeting Proteins

| Targeting Protein | Targeted Cell Type | Size (kDa) | Approximate affinity (Kd in nM) |
|---|---|---|---|
| DARPin G3-HAVD | HER2+ | 17 | 269 |
| DARPin H6-3-B3 | HER2+ | 17 | 28 |
| DARPin H10-2-G3 | HER2+ | 17 | 0.09 |

The affinity of the targeting protein for binding the targeting moiety may vary within a range as defined by the dissociation constant $K_d$ and limited by one or more of at least several considerations. If the binding affinity of a targeting protein is too low, the split supercharged reporter may not preferentially bind to the targeted cell, and/or the targeted cell may be unable to retain the split supercharged reporter for a time sufficient to allow the reassembly of the supercharged reporter protein. By contrast, if the binding affinity of a targeting protein is too high, the split supercharged reporter will preferentially bind to the targeted cell, but the individual elements of the split supercharged reporter may be sequestered on spatially separated targeting moieties and/or in unfavorable orientations for reassembly, thereby inhibiting the reassembly of the reporter fragments into the supercharged reporter protein. In an aspect, the binding affinity of the targeting protein is sufficiently high to allow the split supercharged reporter to bind preferentially to the targeted cell, but also sufficiently low to allow individual targeting proteins to reversibly release from one individual targeting moiety and re-bind to a different individual targeting moiety situated in a different spatial location on the targeted cell. In this aspect, the binding affinity is sufficient to maintain a relatively high concentration of C-terminal reporter fragments and the N-terminal reporter fragments on the surface of the targeted cell, while permitting limited mobility of the reporter fragments to facilitate the reassembly of the supercharged reporter protein. In one aspect, the dissociation constant for a targeting protein-targeting moiety interaction may range from about 0.01 nM to about 100,000 nM.

The overall size of the targeting proteins may vary anywhere within a range limited by one or more of at least several considerations. In one aspect, the targeting protein may be sufficiently large to bind selectively to the corresponding targeting moiety. In another aspect, the targeting protein may not be so large that the reassembled supercharged reporter protein, which remains fused with the targeting proteins and possibly the attached targeting moieties, is not inhibited from penetrating into the targeted cell. In an additional aspect, the targeting protein may range from about 1 kDA to about 500 kDa.

Non-limiting examples of suitable targeting moieties include: cell marker proteins, cell surface receptors, and any other known proteins, protein fragments, peptides, antibodies, antibody fragments, or amino acids situated upon or within a cell membrane of the targeted cell. Non-limiting examples of cell marker proteins include CD proteins such as CD3, CD4, CD8, CD11a, CD16, CD25, CD 31, CD34, CD45, CD114, CD182, and Foxp3. Non-limiting examples of cell surface receptors include: peripheral membrane proteins including enzymes, membrane-targeting domains/lipid clamps, structural domains, transporters of small hydrophobic molecules, electron carriers, polypeptide hormones, toxins, and antimicrobial peptides; transmembrane proteins including G protein-coupled receptors, ligand-gated ion channels, and receptor tyrosine kinases (RTKs); and soluble globular proteins including nuclear receptors. Typically, the targeting moiety is overexpressed on the surface of the targeted cell to facilitate preferential binding of the split supercharged reporter to the targeted cell.

In one aspect, the targeting moieties may be detectable markers of cancer stem cells including, but not limited to, cell surface markers which are detectable in specific malignancies. Non-limiting examples of detectable cell surface markers associated with specific malignancies include: bladder cancer stem cell markers such as CD44 and CD47; breast cancer stem cell markers such as aldehyde dehydrogenase 1-AV (ALDH1A1), BMI-1, CD24, CD44, Cd49/Integrin alpha-6, CD126/IL-6R-alpha, CXR1/IL-8 RA, CXCR4, DLL4, EpCAM/TROP1, ErbB2/Her2, GLI-1, GLI-2, and PTEN; colon cancer stem cell markers such as ALDH1A1, CD44, CD26/DPPIV, CD166/ALCAM, EpCAM/TROP1, GLI-1, and Musahi-1; gastric cancer stem cell markers such as A20/TNFAIP3, ABCG2, CD49, CD126, CD171/NCAM-L1, CX3CR1, CXCR4, CX3CL1/fFactalkine, HIF-2-alpha/EPAS1, Mushai-1, c-Myc, Nestin, and Podoplanin; head and neck cancer stem cell markers such as ABCG2, ALDH1A1, BMI-1, and CD44; and leukemia cancer stem cell markers such as BMI-1, CD34. CD38, CD44, CD96, CD117/SCF R/c-kit, CD123/IL-3R-alpha, GLI-1, GLI-2, MICL/CLEC12A, Mushai-2, and TIM-3; liver cancer stem cell markers such as alpha-fetoprotein/AFP, Aminopeptidase N/ANPEP, CD90/Thy1, and NF2/Merlin; lung cancer stem cell markers such as ABCG2, ALDH1A1, CD90/Thy1, CD117/SCF R/c-kit, and EpCAM/TROP1; melanoma cancer stem cells markers such as ABCB5, ABCG2, CD20/MS4A1, CD166/ALCAM, CD271/NGFR/TNFRSF16 and Nestin; myeloma cancer stem cell markers such as CD19, CD20/MS4A1, CD27/TNFRSF7, CD38, and CD138/Syndecan-1; osteosarcoma stem cell markers such as ABCG2, Nestin and STR)-1; ovarian cancer stem cell markers such as CD44 and CD117/SCF R/c-kit; pancreatic cancer stem cell markers such as BMI-1, CD24, CD44, CXCR4 and EpCAM/TROP1; prostate cancer stem cell markers such as ABCG2, BMI-1, CD44, c-Myc and Integrin alpha2beta1.

In various aspects, the one or more targeting moieties may be selected to enhance the selectivity of binding of the split supercharged reporter to the targeted cell. In one aspect, the C-terminal reporter fragment and the N-terminal reporter fragment may be fused to the same targeting protein which has an affinity for binding a targeting moiety possessed solely by the targeted cell. In another aspect, the C-terminal reporter fragment and the N-terminal reporter fragment may each be fused with a first and second targeting protein, respectively. In this other aspect, the combinations of the first and second targeting moieties to which the first and second targeting proteins preferentially bind are typically found only on the cell membrane of the targeted cell.

In various aspects, the targeting proteins and/or the interacting proteins may be fused to the C-terminal and N-terminal reporter fragments using a linker. The linker may include any peptide sequence with a peptide length ranging from about 2 amino acid residues to about 20 amino acid residues. The length of the linker may be selected to be sufficiently long to permit some degree of flexibility in the orientation of the C-terminal and N-terminal reporter fragments when the attached interacting/targeting proteins are bound to corresponding moieties in order to facilitate the reassembly of the supercharged reporter protein. However, if the length of the linker is too long, the linker may be vulnerable to enzymatic degradation, resulting in an undesired detachment of the reporter fragment from the targeting/interacting protein. Non-limiting examples of suitable linkers include: 8-residue linkers including GGSGSGSS [SEQ ID NO. 7], and GTSGGSG [SEQ ID NO. 8]; and 6-residue linkers including GGTGGS [SEQ ID NO. 9].

Method for Detecting Protein-Protein Interactions

In various aspects, the split supercharged reporter may be used to detect a protein-protein interaction in vivo as described herein above. A flow chart illustrating a method 100 for detecting a protein-protein interaction in one aspect is illustrated in FIG. 1. As summarized in FIG. 1, the method 100 may include providing a split supercharged reporter at step 102. The split supercharged reporter may be derived from any of the supercharged reporter proteins described herein above, resulting in a C-terminal reporter fragment and an N-terminal reporter fragment, also described herein above.

The method 100 further includes fusing the C-terminal reporter fragment with a first interacting protein and fusing the N-terminal reporter fragment with a second interacting protein at step 104. Any known method of protein-protein fusion may be used to fuse the interacting protein with its corresponding reporter fragment. Non-limiting examples of genetic engineering techniques suitable for fusing a reporter fragment to an interacting protein include ligation techniques such as chemical ligation and native ligation, and overlap extension PCR. In one aspect, a linker, described herein previously, may be inserted between the interacting protein and the reporter fragment.

The method 100 further includes introducing the fused reporter fragments and interacting proteins into a cell at step 106. The introduction of the fused protein may be accomplished using any technique known in the art. In one aspect, the fused protein may be provided in the form of a nucleic acid sequence encoding the fused protein. In this aspect, the nucleic acid sequence may be incorporated into a vector in order to transport the nucleic acid sequence into the cell. Non-limiting examples of suitable vectors include plasmids and viral vectors. For example, a first nucleic acid sequence encoding the first interacting protein may be cloned into a first plasmid along with a second nucleic acid sequence encoding the C-terminal reporter fragment. A second plasmid may be similarly modified to incorporate a third nucleic acid sequence encoding the N-terminal reporter fragment and a fourth nucleic acid sequence encoding the second interacting protein. The modified first plasmids and second plasmids may be introduced into a bacterial cell.

The method 100 further includes incubating the cells containing the fused reporter fragments and interacting proteins at step 108. If the fused protein was provided in the form of a nucleic acid sequence, the incubation of the cells induces expression of the introduced nucleic acid sequences, resulting in the production of the fused proteins of the split supercharged reporter described herein above. As production of the fused production continues during cell incubation, the concentration of the fusion proteins of the split supercharged reporter gradually increases. At a sufficiently high concentration, depending on the affinity of the interacting proteins, the reporter fragments may irreversibly reassemble into functional supercharged reporter proteins, resulting in the production of a reporter signal as described herein above.

The method further includes measuring the reporter signal at step 110. The reporter signal may include any of the reporter signals described herein above including fluorescence, catalyzing a fluorescent or colorimetric reaction, or imparting immunity to an exotoxin. The reporter signal may be measured using any known method including, but not limited to: measuring fluorescence intensity using flow cytometry, fluorescent microscopy, or any other known method; measuring color intensity using flow cytometry or any other known method; counting colonies; and/or measuring colony sizes.

In one aspect, the supercharged reporter protein may be a superpositive green fluorescent protein (spGFP). As described herein above, the use of spGFP has several significant advantages over other existing reporter proteins including enhanced solubility and resistance to aggregation within the cell at physiological temperatures, thereby facilitating the detection of protein-protein interactions due to the elevated availability of reporter fragment-interacting protein fusion proteins for reassembly and subsequent signaling. In addition, because the reassembly of the split spGFP is irreversible, the concentration of functional spGFP increases over time, resulting in the detection of relatively weak protein-protein interactions.

Method for Detecting Targeted Cells

Figure 2:
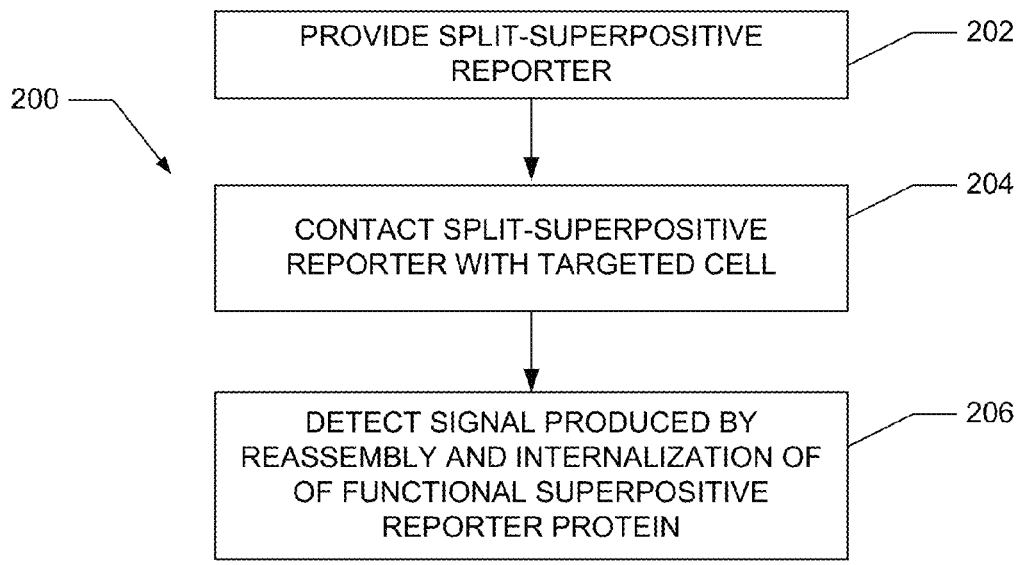
FIG. 2 is a flow chart summarizing a method of detecting a targeted cell using a split-supercharged reporter.

In various aspects, the split supercharged reporter may be used to detect a targeted cell in vivo as described herein above. A flow chart illustrating a method 200 for detecting a protein-protein interaction in one aspect is illustrated in FIG. 2. As summarized in FIG. 2, the method 200 may include providing a split supercharged reporter at step 202. In this aspect, the split supercharged reporter may be derived from any of the supercharged reporter proteins described herein above, resulting in a C-terminal reporter fragment and an N-terminal reporter fragment. The split supercharged reporter includes the C-terminal reporter fragment fused with a first targeting protein and the N-terminal reporter fragment fused with a second targeting protein as described herein above. The split supercharged reporter is typically provided in the form of proteins rather than in the form of nucleic acids. The split supercharged protein may be produced using any known production method for bioengineered proteins.

For example, nucleic acid sequences encoding the C-terminal reporter and the first targeting protein may be cloned into a plasmid, and the plasmid may be introduced into a bacterial cell. The bacterial cell may be incubated to produce a fused protein containing the C-terminal reporter fragment and the first targeting protein within the bacterial cell. The fused protein containing the N-terminal reporter fragment and the second targeting protein may be similarly produced, albeit within a separate bacterial cell to avoid inadvertent reassembly of the reporter fragments into the supercharged reporter protein.

The method 200 further includes contacting the two fusion proteins of the split superpositive reporter with the targeted cell at step 204. In one aspect, the split superpositive reporter may be contacted with an in vitro culture containing the targeted cells by adding a solution containing the suspended split superpositive reporter to the culture medium. In another aspect, the split superpositive reporter may be contacted with the targeted cells in vivo by any known means of administration associated with the introduction of therapeutic or diagnostic compounds into a mammalian organism. In one aspect, split superpositive reporter may be suspended in an aqueous solution including, but not limited to a buffered sucrose solution, a buffered saline solution, a sterile aqueous solution, or any other known solutions suitable for administration to mammalian subjects. Non-limiting examples of suitable means of administration of the split superpositive reporter include: intravenous injections, intramuscular injections, intraperitoneal injections, intraventricular injections, oral administration, transdermal administration, transmucosal administration, and any other known suitable means of administration.

Once the split superpositive reporter is contacted with the targeted cells, the first and second targeting proteins fused with the reporter fragments may reversibly bind to the corresponding first and second targeting moieties overexpressed on the surface of the targeted cells, as described herein above. Individual fused proteins may detach and reattach to differently located and oriented targeting moieties. Over time, a first fused protein containing a C-terminal reporter fragment and a second fused protein containing an N-terminal reporter fragment may reattach at a favorable separation and relative orientation for the reassembly of the reporter fragments into a functional superpositive reporter protein. The folded conformation of the functional superpositive reporter protein, along with the protein's relatively large net positive theoretical charge, induces the penetration of the functional superpositive reporter protein into the inside of the targeted cell, as described herein previously. Because the reassembly of the functional superpositive reporter protein is irreversible, the concentration of functional superpositive reporter proteins, and the magnitude of the associated reporting signal generated within the targeted cell, gradually increase over time.

The method 200 further includes detecting the signal produced by the functional superpositive reporter protein from within the targeted cell at step 206. The signal may include any of the signals described herein above including fluorescence, catalyzing a fluorescent or colorimetric reaction, or imparting immunity to an exotoxin. The signal may be measured using any known method including, but not limited to: measuring fluorescence intensity using flow cytometry, fluorescent microscopy, or any other known method; measuring color intensity using flow cytometry or any other known method; counting colonies; and/or measuring colony sizes.

In one aspect, the signal produced by the functional superpositive reporter protein within the targeted cell may be detectable as early as one hour after the contact of the split superpositive reporter with the targeted cell at step 204. In other aspects, the signal produced by the functional superpositive reporter protein within the targeted cell may be detectable within one hour, within one hour, within two hours, within three hours, within four hours, within five hours, within six hours, within seven hours, within eight hours, within nine hours, within ten hours, within twelve hours, within fourteen hours, within sixteen hours, within twenty hours, or within twenty-four hours after the contact of the split superpositive reporter with the targeted cell at step 204. In another aspect, the maximum intensity of the signal produced by the functional superpositive reporter protein may occur at about 12 hours after the contact of the split superpositive reporter with the targeted cell at step 204.

Because the only functional superpositive reporter proteins are internalized within the targeted cells, images may be obtained without washing cells, and no appreciable background signal is generated. This feature is unique to the "turn-on" targeted cell detection reported protein described herein previously. Fluorescence or other reporting signals are derived only as a result of targeting cell-mediated split superpositive reporter reassembly.

In one aspect, the superpositive reporter protein may be a superpositive green fluorescent protein (spGFP). As described herein above, the use of spGFP has several significant advantages over other existing reporter proteins including enhanced solubility and resistance to aggregation within the cell at physiological temperatures, thereby facilitating the detection of protein-protein interactions due to the elevated availability of reporter fragment-interacting protein fusion proteins for reassembly and subsequent signaling. In addition, the combined high positive net theoretical charge of the reassembled spGFP, combined with the folded structure of reassembled spGFP, result in the ready penetration of the reassembled spGFP into the targeted cell, also described previously herein. Because the reassembly of the split spGFP is irreversible, the concentration of functional spGFP within the targeted cell increases over time, permitting in the detection of relatively weak protein-protein interactions.

In another aspect, the superpositive reporter protein may be a superpositive red fluorescent protein (sp-mNeptune). The mNeptune protein, described herein above, is an analog of superpositive green fluorescent protein, and possesses all of the advantageous characteristics of spGFP described herein previously. In addition, sp-mNeptune fluoresces when excited by light at a wavelength of 633 nm commonly used for the imaging of deep tissues in mammalian subjects. In this other aspect, the use of sp-mNeptune makes possible the detection of targeted cells in deep tissues using the methods described herein previously.

It is to be understood that there is no intention to limit the invention to the forms described in any section of the present disclosure including the Drawings, Summary of the Invention or the Detailed Description. One skilled in the art will recognize that there are numerous modifications, equivalents and alternative constructions that fall within the spirit and scope of the disclosure and the invention as expressed in the claims.

EXAMPLES

The following examples are included to demonstrate various aspects of the disclosure. It should be appreciated by those of skill in the art that the techniques disclosed in the examples that follow represent techniques discovered to function well in the practice of the disclosure, and thus can be considered to constitute preferred modes for its practice. However, those of skill in the art should, in light of the present disclosure, appreciate that many changes can be made in the specific aspects which are disclosed and still obtain a like or similar result without departing from the spirit and scope of the disclosure.

Example 1

Plasmid Construction

The plasmids used in Examples X-Y were either obtained from outside sources, or constructed using the following procedures.

pET11a-Z-Nsg100GFP and pMRBAD-Z'-Csg100GFP plasmids were obtained from an outside source. The pET11a-Z-Nsg100GFP plasmid included nucleic acid sequences encoding the N-terminal fragment of the stabilized GFP variant g100 (Nsg100GFP) and one of the antiparallel leucine zipper proteins (Z). The pMRBAD-Z'-Csg100GFP plasmid included nucleic acid sequences encoding the C-terminal fragment of the stabilized GFP variant g100 (Csg100GFP) and the partner protein of the antiparallel leucine zipper proteins (Z').

pET11a-Z-NfrGFP and pMRBAD-Z'-CfrGFP plasmids were also obtained from an outside source. The pET11a-Z-NfrGFP plasmid included nucleic acid sequences encoding the N-terminal fragment of the folding reporter GFP variant (NfrGFP) and one of the antiparallel leucine zipper proteins (Z). The pMRBAD-Z'-CfrGFP plasmid included nucleic acid sequences encoding the C-terminal fragment of the folding reporter GFP variant (CfrGFP) and the partner protein of the antiparallel leucine zipper proteins (Z').

To construct the plasmids encoding the fusion proteins that included the C-terminal or N-terminal fragments of the superpositive green fluorescent protein variant (spGFP) fused to the proteins of the anti-parallel leucine zipper pair (Z/Z'), the following procedure was performed.

The nucleic acid sequence encoding the superpositive green fluorescent protein (spGFP) was constructed using overlap PCR, amplified with 5'-CATGCCATGGT-TATGGGTCATCACCACCACCA-3' (forward primer, SEQ ID NO. 10) and 5'-GGGGTACCCTTGTAGCGT-TCGTCGCGTC-3' (reverse primer, SEQ ID NO. 11), and cloned into the NcoI and KpnI sites of a pET plasmid.

From this DNA, a DNA sequence encoding the N-terminal fragment of spGFP (encoding amino acids 1-157) was amplified by PCR using 5'-GGAATTCCATATGGGTCATCAC-CACCACCATC-3' (forward primer for the N-terminal fragment, SEQ ID NO. 12) and 5'-CCGCTCGAGCCAGAGCCAGAGCCAC-CGCGTTTATCGGCCGTAAATTACACCTTA TGAG-3' (reverse primer for the N-terminal fragment, SEQ ID NO. 13). This amplicon was double digested with NdeI and BamH1 and cloned into pET11a-Z-NGFP, replacing NGFP (sg100), to create the new construct pET11a-Z-NspGFP.

The C-terminal fragment (CspGFP) was amplified from pET-spGFP using 5'-TTTAGACGTCGGGTGGAAGCGG-TAAGAATGGTATCAAGGCAAAATTCAAAATTCG C-3' (forward primer for the C-terminal fragment, SEQ ID NO. 14) and 5'-TTA TCATGTACATTACTTGTAGCGT-TCGTCGCGTCC-3' (reverse primer for the C-terminal fragment, SEQ ID NO. 15). This amplicon was double digested with NcoI and BsrG1 and cloned into pMRBAD-Z'-CGFP, replacing CGFP, to create the new construct pMRBAD-Z'-CspGFP.

To construct the plasmids encoding the fusion proteins that included the C-terminal or N-terminal fragments of the superpositive green fluorescent protein variant (spGFP) fused to the proteins of the Pdar/Prb reacting pair, the following procedure was performed.

Plasmids encoding Pdar and Prb were obtained from an outside source. Pdar was amplified using 5'-CATGCCATG-GCAAGCGATCTGGGTAAA AAGCTGCT-3' (forward primer, SEQ ID NO. 16) and 5'-ATATAGACGTCTTGCAG-GATCTCTGCCAGATCTTC-3' (reverse primer, SEQ ID NO. 17), double digested with NcoI and AatII and cloned into pMRBAD-Z'-CspGFP replacing Z', to create the new construct pMRBAD-Pdar-CspGFP. Prb was amplified using 5'-CCGCTCGAGGGCAGCACCCGTCCG-3' (forward primer, SEQ ID NO. 18) and 5'-ATATGGATCCTTAC-TATTTTTCGCCCAGCAGGC-3' (reverse primer, SEQ ID NO. 19), double digested with XhoI and BamHI and cloned into pET11a-Z-NspGFP, replacing Z, to create the new construct pET11a-Prb-NspGFP.

To construct the plasmids encoding the fusion proteins that included the C-terminal or N-terminal fragments of the folding reporter GFP variant (frGFP) fused to the proteins of the Pdar/Prb reacting pair, the following procedure was performed.

Pdar was again amplified using 5'-CATGCCATG-GCAAGCGATCTGGGTAAA AAGCTGCT-3' (forward primer, SEQ ID NO. 16) and 5'-ATATAGACGTCTTGCAG-GATCTCTGCCAGATCTTC-3' (reverse primer, SEQ ID NO. 17), double digested with NcoI and AatII and cloned into pMRBAD-Z'-CfrGFP replacing Z', to create the new construct pMRBAD-Pdar-CfrGFP. Prb was amplified using 5'-CCGCTCGAGGGCAGCACCCGTCCG-3' (forward primer, SEQ ID NO. 18) and 5'-ATATGGATCCTTAC-TATTTTTCGCCCAGCAGGC-3' (reverse primer, SEQ ID NO. 19), double digested with XhoI and BamHI and cloned into pET11a-Z-NfrGFP, replacing Z, to create the new construct pET11a-Prb-NfrGFP.

Example 2

Generation, Growth and Induction of E. coli Expressing Split-GFP Positive Control Plasmids To co-transform compatible pairs of plasmids (pET11a-Z-NGFP/pMRBAD-Z-CGFP, pET11a-Z-NfrGFP/pMRBAD-Z-CfrGFP, or pET11a-Z-NspGFP/pMRBAD-Z-CspGFP), the following procedures were performed.

A construct containing the N-terminal fragment was transformed into chemically competent BL21 (DE3) E. coli using a standard heat-shock protocol. These cells were then transformed with the construct containing the respective complementary C-terminal fragment using electroporation. Expression of split-GFP fragments was accomplished by first growing cells overnight to saturation at 37° C. in LB supplemented with 100 mg mL-1 ampicillin and 35 mg mL-1 kanamycin. Overnight cultures were diluted 1:100 into fresh LB supplemented with 100 mg mL-1 ampicillin and 35 mg mL-1 kanamycin. Cultures were monitored by optical density and induced at OD600≈0.60 using 10 µM IPTG and 0.2% (L)-arabinose. All protein expression experiments performed on agar plates were carried out following standard protocols.

Example 3

The Efficiency of Split-Sg100 GFP and Split-spGFP Reassembly were Compared Using Antiparallel Leucine Zipper Peptides BL21 E. coli were co-transformed with pET11a-Z-NGFP and pMRBAD-Z-CGFP, where Z was the positive control leucine zipper peptide and GFP was an N- or C-terminal fragment of either sg100GFP or spGFP. In order to compare the maximum cell fluorescence generated as a result of split-GFP reassembly, E. coli were induced to express the split-GFP-Z fusions with IPTG and arabinose and incubated at 25° C. E. coli samples were prepared for flow cytometry by centrifugation and resuspension in phosphate buffered saline (PBS) and analyzed by flow cytometry using a MoFlo (Dako Colorado, Inc.) flow cytometer illuminated by a solid-state iCyt 488 nm laser.

Figure 3:
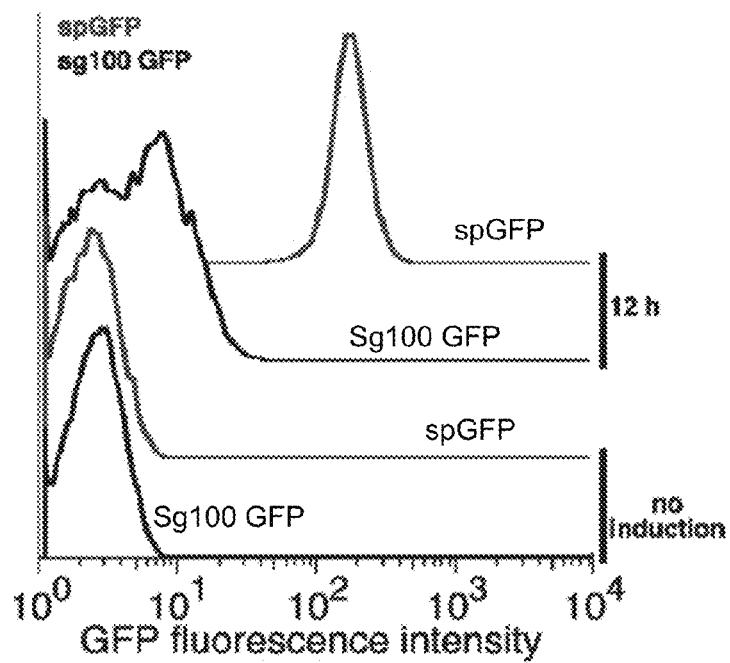
FIG. 3 is a graph comparing GFP fluorescence after 12 hours of incubation at a temperature of 25° C. measured from *E. coli* expressing split spGFP and split sg100 GFP reporters fused with antiparallel leucine zipper proteins.

For both systems, maximum cell fluorescence was reached after 12 hours. After 12 hours the mean cellular fluorescence in E. coli expressing the split-spGFP positive control fragments increased 75-fold compared to uninduced cells, while mean cellular fluorescence in E. coli that expressed the split-sg100 GFP positive control fragments only increased 2.3-fold, and fluorescence distribution was broad, as illustrated in FIG. 3. When E. coli containing each set of positive control plasmids were incubated at 30° C. for 18 hours, a much higher level of cell fluorescence was easily observed visually in E. coli expressing the split-spGFP positive controls. E. coli containing the split-sg100 GFP or split-spGFP constructs did not generate significant cell fluorescence in the absence of IPTG and arabinose induction reagents, as illustrated in FIG. 3.

Taken together, these results clearly show that split-spGFP reassembly is much more efficient than split-sg100 GFP reassembly. This 72.8-fold increase in cell fluorescence drastically simplifies the identification of interacting pairs when using either flow cytometry or by picking fluorescent colonies. E. coli expressing split-spGFP fragments fused to non-interacting pairs don't evolve any significant fluorescence.

Example 4

The Time-Dependence of Split-Sg100 GFP and Split-spGFP Reassembly were Compared Using Antiparallel Leucine Zipper Peptides The time-dependence of split-GFP reassembly was measured in E. coli that expressed the split-sg100 GFP or split-spGFP positive control plasmids. E. coli was induced, incubated at 25° C., and cell fluorescence was measured by flow cytometry after 1, 2, and 3 hours using methods similar to those described in Example 3.

Figure 4A:
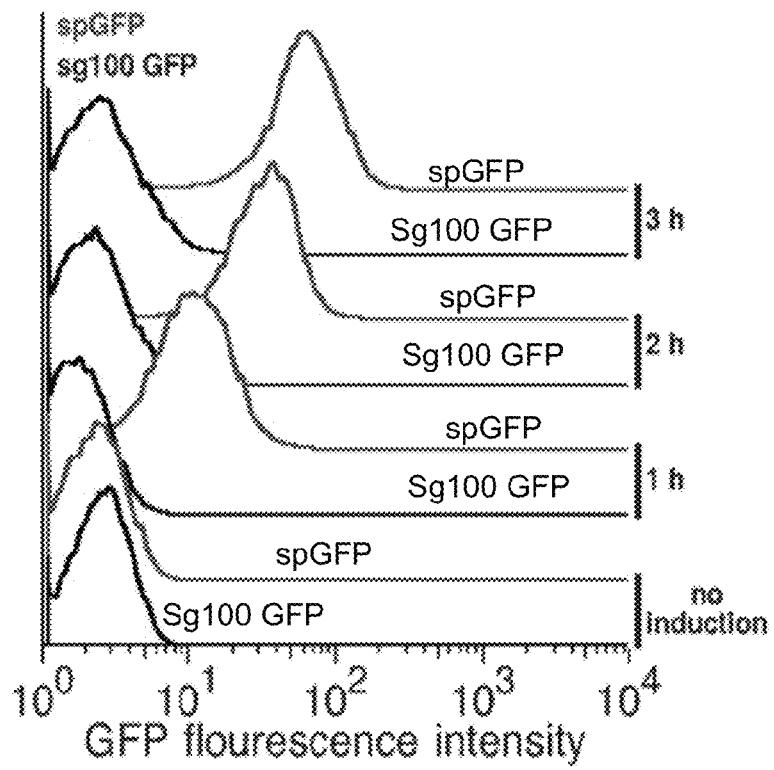
FIG. 4A is a graph comparing GFP fluorescence after 1, 2, and 3 hours of incubation at a temperature of 25° C. measured from *E. coli* expressing split spGFP and split sg100 GFP reporters fused with antiparallel leucine zipper proteins.
Figure 4B:
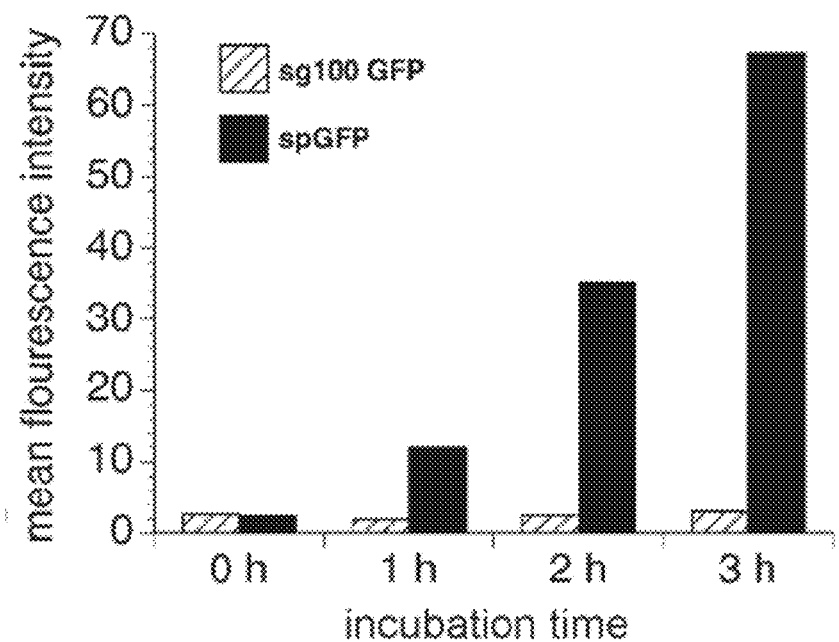
FIG. 4B is a bar chart summarizing the mean fluorescent intensities obtained from an analysis of the graphs of FIG. 4A.

The results of these experiments are summarized in FIGS. 4A and 4B. One hour after incubation no appreciable increase in cell fluorescence was observed in E. coli expressing the split-sg100 Z peptide positive control fusions. In contrast, after the same period of time, a 5-fold increase in mean cell fluorescence was observed in E. coli expressing the split-spGFP positive control fusions. After two hours, no appreciable change in fluorescence was observed in E. coli expressing the split-sg100 GFP leucine zipper fusions, while a 15-fold change was observed for the split-spGFP system. Three hours after induction, a very modest 1.2-fold increase in mean cell fluorescence was observed in as a result of split-sg100 GFP reassembly. After the same period of time, a 28-fold increase in mean cell fluorescence was observed in E. coli expressing the split-spGFP positive controls.

Taken together, these data show that split-spGFP reassembly drastically shortens the experimental time needed to visualize and identify an in vivo interaction. Interaction-dependent changes in cell fluorescence as a result of split-spGFP reassembly were easily observed by flow cytometry in as little as one hour.

Example 5

The Efficiency and Time-Dependence of Split-frGFP and Split-spGFP Reassembly were Compared To compare the efficiency and time-dependence of GFP evolution for split-frGFP and split-spGFP using flow cytometry, the following experiments were conducted.

Split-folding reporter-GFP (split-frGFP) is constructed from a GFP variant optimized to fold robustly. When fused to antiparallel leucine zipper peptides, split-frGFP reassembly was qualitatively determined to be significantly faster and more efficient than split-sg100 GFP reassembly.

E. coli that expressed the split-frGFP or split-spGFP positive control plasmids was induced, incubated at 25° C., and cell fluorescence was measured by flow cytometry after 1 hour, 2 hours, 3 hours, and 12 hours using methods similar to those described in Example 3.

Figure 5A:
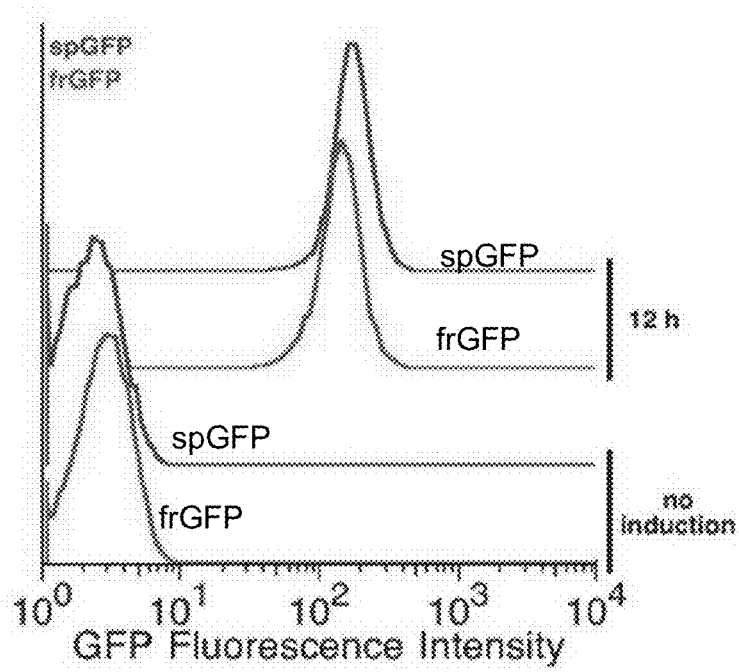
FIG. 5A is a graph comparing GFP fluorescence after 12 hours of incubation at a temperature of 25° C. measured from E. coli expressing split spGFP and split frGFP reporters fused with antiparallel leucine zipper proteins.
Figure 5B:
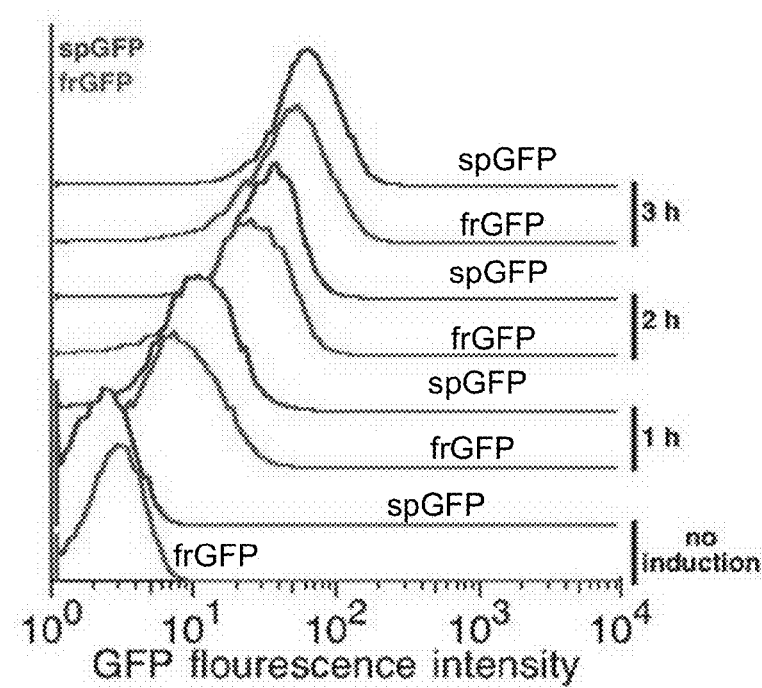
FIG. 5B is a graph comparing GFP fluorescence after 1, 2, and 3 hours of incubation at a temperature of 25° C. measured from E. coli expressing split spGFP and split frGFP reporters fused with antiparallel leucine zipper proteins.

As shown in FIG. 5A, when incubated at 25° C. for 12 hours, which was when maximum fluorescence is observed for both systems, E. coli expressing the split-frGFP and split-spGFP positive control leucine zipper fusions both exhibit high levels of cell fluorescence. However, maximum mean cell fluorescence was 22% brighter in E. coli expressing the split-spGFP positive controls, also shown in FIG. 5A. As seen in FIG. 5B, reassembly of the split-spGFP positive controls was faster than reassembly of split-frGFP. One hour after induction, E. coli expressing the split-spGFP positive control fusions was 34% more fluorescent than cells expressing the split-frGFP fusions.

Example 6

The Efficiency of Split-frGFP and Split-spGFP Reassembly at 37° C. was Compared

Reassembly systems that operate efficiently at 37° C. are ideal, since interactions identified at this temperature are more likely to occur in their native physiological context. The efficiency of split-spGFP reassembly in E. coli incubated at 37° C. was compared to the efficiency of reassembly of split-frGFP using methods similar to those described in Example 5.

Figure 6:
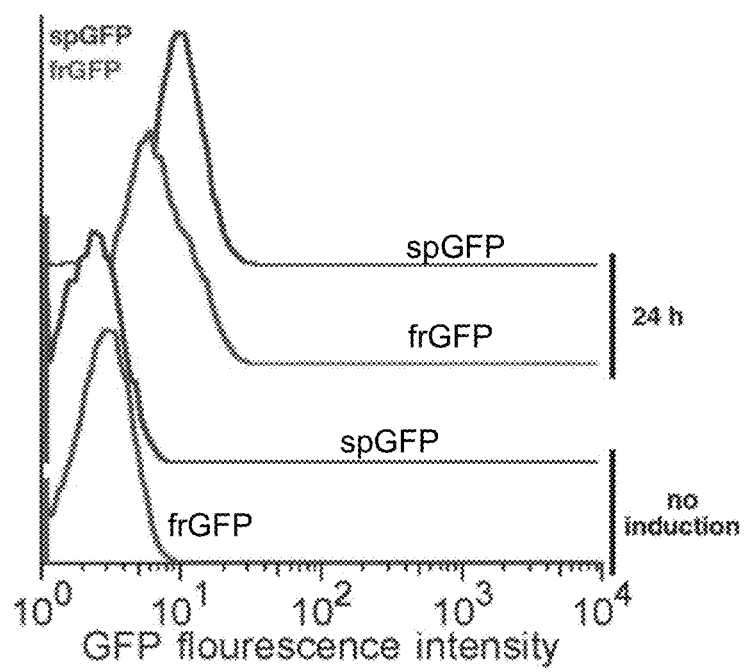
FIG. 6 is a graph comparing GFP fluorescence after 24 hours of incubation at a temperature of 37° C. measured from E. coli expressing split spGFP and split sg100 GFP reporters fused with antiparallel leucine zipper proteins.

As shown in FIG. 6, interaction-dependent split-spGFP reassembly was significantly more efficient than split-frGFP reassembly at 37° C. When incubated for 24 hours, E. coli expressing the split-spGFP positive control antiparallel leucine zipper fusions was 24% more fluorescent than cells expressing the split-frGFP fusions. The significant increase in split-spGFP reassembly efficiency at 37° C. demonstrated the robustness of this reporter system and provided evidence for its use in identify interactions at physiological conditions.

Example 7

The Efficiency and Time-Dependence of Detecting a Protein—Protein Interaction was Compared Using Split-frGFP and Split-spGFP To compare the efficiency of protein-protein interaction detection using split-spGFP and split-frGFP for protein-protein interactions that are less than ideally aligned, the following experiments were conducted.

N- and C-terminal fragments of spGFP and frGFP were fused to Pdar and Prb, a high-affinity de novo designed protein—protein interaction as described in Example 1. E. coli expressing either N-spGFP-Prb/C-spGFP-Pdar or N-frGFP-Prb/C-frGFP-Pdar were induced with IPTG and arabinose, and Pdar/Prb interaction-dependent cell fluorescence was monitored at 37° C. by flow cytometry using methods similar to those described in Example 6.

Figure 7A:
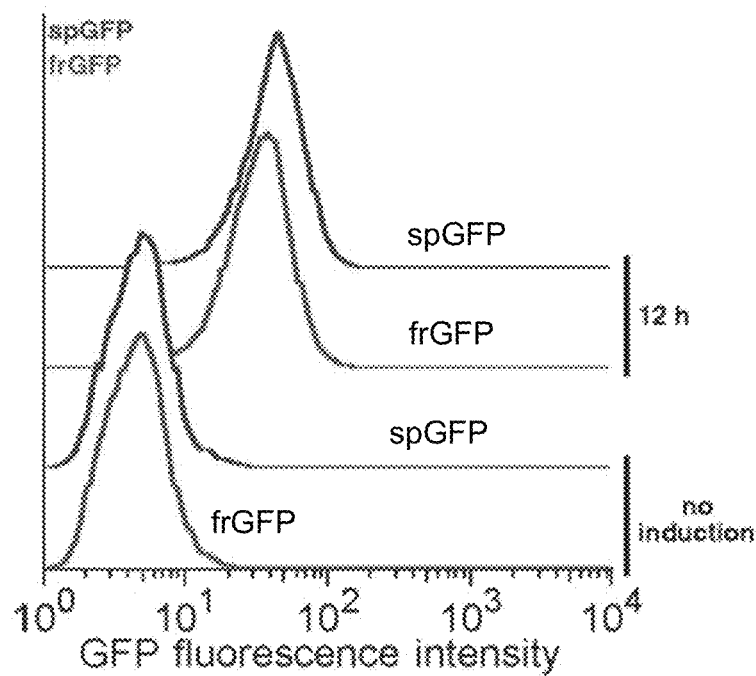
FIG. 7A is a graph comparing GFP fluorescence after 12 hours of incubation at a temperature of 37° C. measured from E. coli expressing split spGFP and split frGFP reporters fused with Prb/Pdar interacting proteins.
Figure 7B:
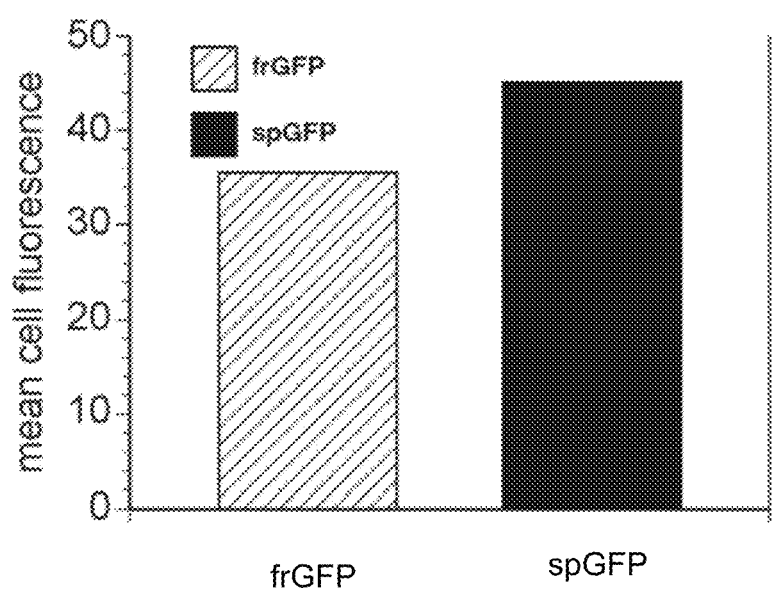
FIG. 7B is a bar chart summarizing the mean fluorescent intensities obtained from an analysis of the graphs of FIG. 7A.

For both split-GFP systems, maximum cell fluorescence was reached after 12 hours. Cells expressing the split-spGFP Pdar/Prb fusions were 27% more fluorescent than cells expressing the split-frGFP Pdar/Prb fusions as summarized in FIGS. 7A and 7B. This significant increase in cell fluorescence showcases the increased efficiency, utility, and robustness of split-spGFP reassembly.

Example 8

Targeted Cells were Detected Using Split-spGFP Reporter Fused to Targeting Proteins To demonstrate the feasibility of selectively detecting a targeted cell using the split-spGFP reporter, the following experiments were conducted.

Using methods similar to those described in Example 1, split-spGFP N-terminal fragments and C-terminal fragments were fused with a previously reported 12-amino acid linear peptide (N-FRPNRAQDYNTN-C, SEQ. ID. NO. 2) that potently binds, but does not appreciably penetrate, PC-3 prostate cancer cells. The resulting split-spGFP reporter was incubated at a concentration of 10 nM with a culture containing PC-3 cells. As a control, the split-spGFP reporter was incubated at a concentration of 10 nM with a culture containing HeLa cells. The cultures were observed using fluorescent microscopy immediately after the introduction of the split-spGFP reporter. No washing of the cells was performed after the introduction of the split-spGFP reporter and subsequent observation of the cultured cells.

Internalized fluorescent punctate corresponding to the reassembled and internalized spGFP was observed inside PC-3 cells as early as 2 minutes after the addition of the split-spGFP reporter. This internalized fluorescent punctate increased significantly over the ten minutes that the PC-3 cells were observed. In addition, essentially no background fluorescence was observed outside of the PC-3 cells. By contrast, no internalized fluorescent punctate or background fluorescence was observed at any time in the culture containing HeLa cells.

The results of this experiment demonstrated that the split-spGFP reporter may be used to selectively detect a targeted cell.

Example 9

A Far-Red Fluorescent Protein May be Supercharged to Develop a Novel Split-Superpositive Far-Red Fluorescent Protein Targeted Cell Detection Platform To develop a novel split-superpositive far-red fluorescent protein targeted cell detection platform, the following procedures may be performed.

mNeptune, a monomeric auto fluorescent far-red protein that is structurally related to GFP, may be mutagenized to develop a superpositive mNeptune (+35_mNep). Methods analogous to the methods used to develop superpositive GFP may be used to mutagenize solvent exposed residues of the existing mNeptune protein (−4_mNep) to produce +35_mNep as summarized in the sequence listings provided in FIG. 8. The +35_mNep may be split into an N-terminal fragment and a C-terminal fragment and fused with targeting proteins using methods similar to the methods described in Examples 1 and 8.

What is claimed is:

1. A method of detecting a targeted cell, the method comprising: providing a split-supercharged reporter comprising a C-terminal reporter fragment fused to a first targeting protein and an N-terminal reporter fragment fused to a second targeting protein; contacting the split supercharged reporter with the targeted cell; detecting a signal produced by a reassembly of the split-supercharged reporter on a surface of the targeted cell.

2. The method of claim 1, wherein the reassembly of the split-supercharged reporter occurs when the first targeting protein binds to a first targeting moiety situated on a surface of the targeted cell, and the second targeting protein binds to a second targeting moiety situated on the surface of the targeted cell.

3. The method of claim 2, wherein the first targeting moiety and the second targeting moiety are different cell surface structures selected from: a membrane receptor, a membrane transport protein, a membrane enzyme, a cell adhesion molecule, and a cell wall structural compound.

4. The method of claim 3, wherein the first targeting protein binds specifically to the first targeting moiety and the second targeting protein binds specifically to the second targeting moiety.

5. The method of claim 4, wherein the combination of the first targeting moiety and the second targeting moiety specifically identify the targeted cell.

6. The method of claim 1, wherein the reassembly of the split-supercharged reporter comprises fusing the C-terminal reporter fragment and the N-terminal reporter fragment to form a functional supercharged reporter protein.

7. The method of claim 6, wherein the functional supercharged reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune).

8. The method of claim 7, wherein the functional supercharged reporter protein is a spGFP, the C-terminal reporter fragment is a C-terminal spGFP fragment and the N-terminal reporter fragment is an N-terminal spGFP fragment.

9. The method of claim 8, wherein: the C-terminal spGFP fragment and the N-terminal spGFP fragment are situated on surface of the targeted cell membrane prior to reassembly of the spGFP; and the spGFP is transferred into a cytoplasm of the targeting cell after reassembly on the surface of the targeted cell.

10. The method of claim 9, wherein: the C-terminal spGFP fragment further comprises a theoretical net charge ranging from about +5 to about +30; the N-terminal spGFP fragment further comprises a theoretical net charge ranging from about +5 to about +30; and the reassembled spGFP further comprises a theoretical net charge ranging from about +5 to about +30.

11. The method of claim 1, wherein the targeted cell is a cancer cell chosen from: a cholangiocarcinoma cell, a prostate cancer cell, a breast cancer cell, a neuroblastoma cell, an osteosarcoma cell, a head cancer cell, a neck cancer cell, and a breast cancer cell.

12. The method of claim 1, wherein the targeted cell is chosen from: a HER-2 positive breast cancer cell and a PC-3 human prostate cancer cell.

13. A split supercharged reporter, the split supercharged reporter comprising a C-terminal reporter fragment fused to a first targeting protein and an N-terminal reporter fragment fused to a second targeting protein.

14. The reporter of claim 13, wherein the first targeting protein and the second targeting protein bind specifically to a targeting moiety situated on a surface of a targeted cell.

15. The reporter of claim 13, wherein the split supercharged reporter reassembles into a functional supercharged reporter protein when the first targeting protein and the second targeting protein bind to a targeting moiety.

16. The reporter of claim 15, wherein the functional supercharged reporter protein is chosen from: a superpositive green fluorescent protein GFP (spGFP), a superpositive far-red fluorescent protein (sp-mNeptune), a supernegative green fluorescent protein (snGFP), and a supernegative far-red fluorescent protein (sn-mNeptune).

17. The reporter of claim 16, wherein the functional supercharged reporter protein is a spGFP, the C-terminal reporter fragment is a C-terminal spGFP fragment and the N-terminal reporter fragment is an N-terminal spGFP fragment.

18. The reporter of claim 17, wherein the C-terminal spGFP fragment comprises a theoretical net charge ranging from about +5 to about +30, the N-terminal spGFP fragment comprises a theoretical net charge ranging from about +5 to about +30, and the spGFP comprises a theoretical net charge ranging from about +5 to about +40.

19. The reporter of claim 13, wherein the first targeting protein and the second targeting protein comprise the same amino acid sequence.

20. The reporter of claim 16, wherein the functional supercharged reporter protein is spGFP split into an N-terminal fragment and a C-terminal fragment, wherein the functional supercharged reporter protein comprises a net theoretical charge of +34, the N-terminal fragment comprises a net theoretical charge of +24, and the C-terminal fragment comprises a net theoretical charge of +10.

21. The reporter of claim 16, wherein the functional supercharged reporter protein is spGFP split into an N-terminal fragment comprising a protein sequence of SEQ ID NO. 22 and a C-terminal fragment comprising a protein sequence of SEQ ID NO. 23.

22. The reporter of claim 16, wherein the functional supercharged reporter protein is a sp-mNeptune, the C-terminal reporter fragment is a C-terminal sp-mNeptune fragment and the N-terminal reporter fragment is an N-terminal sp-mNeptune fragment.

23. The reporter of claim 16, wherein the functional supercharged reporter protein is sp-mNeptune comprising a protein sequence of SEQ ID NO. 21 split into an N-terminal fragment comprising and a C-terminal fragment.

* * * * *

SEQUENCE LISTING

<160> NUMBER OF SEQ ID NOS: 23

<210> SEQ ID NO 1
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 1

Thr Pro Val Leu Glu Thr Pro Lys Leu Leu Leu Trp
1               5                   10

```
<210> SEQ ID NO 2
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 2

Phe Arg Pro Asn Arg Ala Gln Asp Tyr Asn Thr Asn
1               5                   10

<210> SEQ ID NO 3
<211> LENGTH: 12
<212> TYPE: PRT
<213> ORGANISM: Artificial Sequence
<220> FEATURE:
<223> OTHER INFORMATION: SYTHENSIZED

<400> SEQUENCE: 3

Val Pro Trp Met Glu Pro Ala Tyr Gln Arg Phe Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 4

Ala Ser Gly Ala Leu Ser Pro Ser Arg Leu Asp Thr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 5

Ala Gly Lys Gly Thr Pro Ser Leu Glu Thr Thr Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 6

Thr Ser Pro Leu Asn Ile His Asn Gly Gln Lys Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 7

Gly Gly Ser Gly Ser Gly Ser Ser
1               5
```

<210> SEQ ID NO 8
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 8

Gly Thr Ser Gly Gly Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 9

Gly Gly Thr Gly Gly Ser
1               5

<210> SEQ ID NO 10
<211> LENGTH: 32
<212> TYPE: DNA
<213> ORGANISM: Artificial Sequence
<220> FEATURE:
<223> OTHER INFORMATION: SYTHENSIZED

<400> SEQUENCE: 10
catgccatgg ttatgggtca tcaccaccac ca                              32

<210> SEQ ID NO 11
<211> LENGTH: 28
<212> TYPE: DNA
<213> ORGANISM: Artificial Sequence
<220> FEATURE:
<223> OTHER INFORMATION: SYNTHESIZED

<400> SEQUENCE: 11
ggggtaccct tgtagcgttc gtcgcgtc                                   28

<210> SEQ ID NO 12
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 12
ggaattccat atgggtcatc accaccacca tc                              32

<210> SEQ ID NO 13
<211> LENGTH: 58
<212> TYPE: DNA
<213> ORGANISM: Artificial Sequence
<220> FEATURE:
<223> OTHER INFORMATION: SYNTHESIZED

<400> SEQUENCE: 13
ccgctcgagc cagagccaga gccaccgcgt ttatcggccg taaattacac cttatgag   58

<210> SEQ ID NO 14
<211> LENGTH: 55
<212> TYPE: DNA
<213> ORGANISM: Artificial Sequence -continued

```
<220> FEATURE:
<223> OTHER INFORMATION: SYNTHESIZED

<400> SEQUENCE: 14
tttagacgtc gggtggaagc ggtaagaatg gtatcaaggc aaaattcaaa attcg         55

<210> SEQ ID NO 15
<211> LENGTH: 36
<212> TYPE: DNA
<213> ORGANISM: Artificial Sequence
<220> FEATURE:
<223> OTHER INFORMATION: SYNTHESIZED

<400> SEQUENCE: 15
ttatcatgta cattacttgt agcgttcgtc gcgtcc                              36

<210> SEQ ID NO 16
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 16
catgccatgg caagcgatct gggtaaaaag ctgct                               35

<210> SEQ ID NO 17
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 17
atatagacgt cttgcaggat ctctgccaga tcttc                               35

<210> SEQ ID NO 18
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 18
ccgctcgagg gcagcacccg tccg                                           24

<210> SEQ ID NO 19
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 19
atatggatcc ttactatttt tcgcccagca ggc                                 33

<210> SEQ ID NO 20
<211> LENGTH: 240
<212> TYPE: PRT
<213> ORGANISM: Artificial Sequence
<220> FEATURE:
<223> OTHER INFORMATION: SYNTHESIZED

<400> SEQUENCE: 20

Met Gly Glu Glu Leu Ile Lys Glu Asn Met His Met Lys Leu Tyr Met
1               5                   10                  15
```

Glu Gly Thr Val Asn Asn His His Phe Lys Cys Thr Ser Glu Gly Glu
         20                  25                  30

Gly Lys Pro Tyr Glu Gly Thr Gln Thr Gly Arg Ile Lys Val Val Glu
         35                  40                  45

Gly Gly Pro Leu Pro Phe Ala Phe Asp Ile Leu Ala Thr Cys Phe Met
     50                  55                  60

Tyr Gly Ser Lys Thr Phe Ile Asn His Thr Gln Gly Ile Pro Asp Phe
65                   70                  75                  80

Phe Lys Gln Ser Phe Pro Glu Gly Phe Thr Trp Glu Arg Val Thr Thr
                 85                  90                  95

Tyr Glu Asp Gly Gly Val Leu Thr Ala Thr Gln Asp Thr Ser Leu Gln
                100                 105                 110

Asp Gly Cys Leu Ile Tyr Asn Val Lys Ile Arg Gly Val Asn Phe Pro
            115                 120                 125

Ser Asn Gly Pro Val Met Gln Lys Lys Thr Leu Gly Trp Glu Ala Ser
130                 135                 140

Thr Glu Thr Leu Tyr Pro Ala Asp Gly Gly Leu Glu Gly Arg Cys Asp
145                 150                 155                 160

Met Ala Leu Lys Leu Val Gly Gly Gly His Leu Ile Cys Asn Leu Lys
                165                 170                 175

Thr Thr Tyr Arg Ser Lys Lys Pro Ala Lys Asn Leu Lys Met Pro Gly
                180                 185                 190

Val Tyr Phe Val Asp Arg Arg Leu Glu Arg Ile Lys Glu Ala Asp Asn
            195                 200                 205

Glu Thr Tyr Val Glu Gln His Glu Val Ala Val Ala Arg Tyr Cys Asp
        210                 215                 220

Leu Pro Ser Lys Leu Gly His Lys Leu Asn Gly Met Asp Glu Leu Tyr
225                 230                 235                 240

<210> SEQ ID NO 21
<211> LENGTH: 240
<212> TYPE: PRT
<213> ORGANISM: Artificial Sequence
<220> FEATURE:
<223> OTHER INFORMATION: SYNTEHSIZED

<400> SEQUENCE: 21

Met Gly Glu Arg Leu Ile Lys Glu Lys Met His Met Lys Leu Tyr Met
1               5                   10                  15

Lys Gly Thr Val Asn Asn His Lys Phe Lys Cys Thr Ser Lys Gly Lys
            20                  25                  30

Gly Lys Pro Tyr Arg Gly Thr Gln Thr Gly Arg Ile Lys Val Val Arg
         35                  40                  45

Gly Gly Pro Leu Pro Phe Arg Phe Asp Ile Leu Ala Thr Cys Phe Met
     50                  55                  60

Tyr Gly Ser Lys Thr Phe Ile Asn Lys Thr Gln Gly Arg Pro Asp Phe
65                   70                  75                  80

Phe Lys Gln Ser Phe Pro Glu Lys Phe Thr Trp Glu Arg Val Thr Thr
                 85                  90                  95

Tyr Glu Lys Gly Gly Val Leu Thr Ala Thr Gln Asp Thr Ser Leu Gln
                100                 105                 110

Asp Gly Cys Leu Ile Tyr Asn Val Lys Ile Arg Gly Val Asn Phe Pro
            115                 120                 125

Ser Asn Lys Pro Val Met Gln Lys Lys Thr Leu Gly Trp Arg Ala Ser
130                 135                 140

```
Thr Lys Thr Leu Tyr Pro Ala Asp Gly Gly Leu Lys Gly Arg Cys Asp
145                 150                 155                 160

Met Lys Leu Lys Leu Val Gly Gly His Leu Ile Cys Asn Leu Lys
            165                 170                 175

Thr Thr Tyr Arg Ser Lys Lys Pro Lys Lys Asn Leu Lys Met Pro Gly
            180                 185                 190

Val Tyr Phe Val Asp Arg Arg Leu Glu Arg Ile Lys Glu Ala Asp Asn
                195                 200                 205

Arg Thr Tyr Val Arg Gln His Glu Val Ala Val Ala Arg Tyr Cys Asp
            210                 215                 220

Leu Pro Ser Lys Leu Gly His Lys Leu Asn Gly Arg Lys Glu Arg Tyr
225                 230                 235                 240

<210> SEQ ID NO 22
<211> LENGTH: 167
<212> TYPE: PRT
<213> ORGANISM: Artificial Sequence
<220> FEATURE:
<223> OTHER INFORMATION: SYNTHESIZED

<400> SEQUENCE: 22

Met Gly His His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Glu Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg
                165

<210> SEQ ID NO 23
<211> LENGTH: 81
<212> TYPE: PRT
<213> ORGANISM: Artificial Sequence
<220> FEATURE:
<223> OTHER INFORMATION: SYNTHESIZED

<400> SEQUENCE: 23

Lys Asn Gly Ile Lys Ala Lys Phe Lys Ile Arg His Asn Val Lys Asp
1               5                   10                  15

Gly Ser Val Gln Leu Ala Asp His Tyr Gln Gln Asn Thr Pro Ile Gly
            20                  25                  30

Arg Gly Pro Val Leu Leu Pro Arg Asn His Tyr Leu Ser Thr Arg Ser
```

```
                35                  40                  45
Lys Leu Ser Lys Asp Pro Lys Glu Lys Arg Asp His Met Val Leu Leu
        50                  55                  60

Glu Phe Val Thr Ala Ala Gly Ile Lys His Gly Arg Asp Glu Arg Tyr
65                  70                  75                  80

Lys
```